United States Patent
Sakamoto et al.

(10) Patent No.: US 9,108,045 B2
(45) Date of Patent: Aug. 18, 2015

(54) METHOD AND APPARATUS FOR OPTICAL INHIBITION OF PHOTODYNAMIC THERAPY

(75) Inventors: Fernanda Hidemi Sakamoto, Boston, MA (US); Richard Rox Anderson, Boston, MA (US); William A. Farinelli, Danvers, MA (US); Apostolos G. Doukas, Belmont, MA (US)

(73) Assignee: The General Hospital Corporation, Boston, MA (US)

(*) Notice: Subject to any disclaimer, the term of this patent is extended or adjusted under 35 U.S.C. 154(b) by 1236 days.

(21) Appl. No.: 12/647,032

(22) Filed: Dec. 24, 2009

(65) Prior Publication Data

US 2010/0174223 A1    Jul. 8, 2010

Related U.S. Application Data

(63) Continuation-in-part of application No. PCT/US2008/068593, filed on Jun. 27, 2008.

(60) Provisional application No. 60/946,536, filed on Jun. 27, 2007.

(51) Int. Cl.
*A61N 5/06* (2006.01)

(52) U.S. Cl.
CPC ..................................... *A61N 5/062* (2013.01)

(58) Field of Classification Search
CPC ............ A61B 18/18; A61B 5/00; A61B 6/00; A61B 19/00
USPC ........................ 606/4; 600/310, 473; 128/898
See application file for complete search history.

(56) References Cited

U.S. PATENT DOCUMENTS

| | | | |
|---|---|---|---|
| 2,469,412 | A | 5/1949 | Roebken |
| 3,942,531 | A | 3/1976 | Hoff et al. |
| 3,991,755 | A | 11/1976 | Vernon et al. |
| 4,141,359 | A | 2/1979 | Jacobsen et al. |

(Continued)

FOREIGN PATENT DOCUMENTS

| | | |
|---|---|---|
| CA | 2190378 A1 | 11/1995 |
| EP | 0 726 083 A2 | 8/1996 |

(Continued)

OTHER PUBLICATIONS

[No Author Listed] Guide for the Care and Use of Laboratory Animals. Committee on Care and Use of Laboratory Animals of the Institute Laboratory Animal Resources Commission on Life Sciences, National Research Council. Published by National Institutes of Health, Bethesda, Maryland, 1985, Publication No. 85-23, 92 pages.

(Continued)

*Primary Examiner* — William Thomson
*Assistant Examiner* — Victor Shapiro
(74) *Attorney, Agent, or Firm* — Nutter McClennen & Fish LLP

(57) ABSTRACT

A system and method are provided for preventing damage to the epidermis or other epithelial or non-target tissue during photodynamic therapy treatment. For example, an inhibiting radiation can be used to control formation of a photosensitizer from a precursor photosensitizer in the epidermis or epithelial tissue. Subsequent application of a treatment radiation can activate the photosensitizer to damage or destroy target sites while the non-target tissue remains substantially unaffected.

20 Claims, 9 Drawing Sheets

(56) References Cited

U.S. PATENT DOCUMENTS

| | | |
|---|---|---|
| 4,250,878 A | 2/1981 | Jacobsen et al. |
| 4,260,630 A | 4/1981 | Bisagni et al. |
| 4,287,554 A | 9/1981 | Wolff |
| 4,395,545 A | 7/1983 | Adam et al. |
| 4,557,723 A | 12/1985 | Sibalis |
| 4,651,739 A | 3/1987 | Oseroff et al. |
| 4,672,969 A | 6/1987 | Dew |
| 4,713,050 A | 12/1987 | Sibalis |
| 4,744,787 A | 5/1988 | Phipps et al. |
| 4,747,819 A | 5/1988 | Phipps et al. |
| 4,752,285 A | 6/1988 | Petelenz et al. |
| 4,803,069 A | 2/1989 | Kekesi et al. |
| 4,827,911 A | 5/1989 | Broadwin et al. |
| 4,854,320 A | 8/1989 | Dew et al. |
| 4,865,582 A | 9/1989 | Sibalis |
| 4,927,408 A | 5/1990 | Haak et al. |
| 4,930,504 A | 6/1990 | Diamantopoulos et al. |
| 4,931,274 A | 6/1990 | Barabino et al. |
| 4,945,908 A | 8/1990 | Schneider |
| 4,950,229 A | 8/1990 | Sage, Jr. |
| 5,019,034 A | 5/1991 | Weaver et al. |
| 5,019,075 A | 5/1991 | Spears et al. |
| 5,022,757 A | 6/1991 | Modell |
| 5,053,033 A | 10/1991 | Clarke |
| 5,080,646 A | 1/1992 | Theeuwes et al. |
| 5,084,006 A | 1/1992 | Lew et al. |
| 5,087,242 A | 2/1992 | Petelenz et al. |
| 5,114,973 A | 5/1992 | Hess et al. |
| 5,116,864 A | 5/1992 | March et al. |
| 5,125,894 A | 6/1992 | Phipps et al. |
| 5,131,403 A | 7/1992 | Haynes |
| 5,135,477 A | 8/1992 | Untereker et al. |
| 5,135,480 A | 8/1992 | Bannon et al. |
| 5,147,296 A | 9/1992 | Theeuwes et al. |
| 5,147,297 A | 9/1992 | Myers et al. |
| 5,158,537 A | 10/1992 | Haak et al. |
| 5,162,042 A | 11/1992 | Gyory et al. |
| 5,162,043 A | 11/1992 | Lew et al. |
| 5,167,616 A | 12/1992 | Haak et al. |
| 5,169,382 A | 12/1992 | Theeuwes et al. |
| 5,169,383 A | 12/1992 | Gyory et al. |
| 5,203,768 A | 4/1993 | Haak et al. |
| 5,207,752 A | 5/1993 | Sorenson et al. |
| 5,209,221 A | 5/1993 | Riedlinger |
| 5,221,254 A | 6/1993 | Phipps |
| 5,226,907 A | 7/1993 | Tankovich |
| 5,232,438 A | 8/1993 | Theeuwes et al. |
| 5,234,940 A | 8/1993 | Kennedy et al. |
| 5,234,992 A | 8/1993 | Gyory et al. |
| 5,236,412 A | 8/1993 | Lloyd et al. |
| 5,240,995 A | 8/1993 | Gyory et al. |
| 5,246,417 A | 9/1993 | Haak et al. |
| 5,246,418 A | 9/1993 | Haynes et al. |
| 5,256,137 A | 10/1993 | Sage, Jr. |
| 5,258,226 A | 11/1993 | Nakagawa et al. |
| 5,281,287 A | 1/1994 | Lloyd et al. |
| 5,284,471 A | 2/1994 | Sage, Jr. |
| 5,288,389 A | 2/1994 | Yamada et al. |
| 5,298,017 A | 3/1994 | Theeuwes et al. |
| 5,302,172 A | 4/1994 | Sage, Jr. et al. |
| 5,304,170 A | 4/1994 | Green |
| 5,306,235 A | 4/1994 | Haynes |
| 5,310,403 A | 5/1994 | Haynes |
| 5,310,404 A | 5/1994 | Gyory et al. |
| 5,312,326 A | 5/1994 | Myers et al. |
| 5,314,502 A | 5/1994 | McNichols et al. |
| 5,320,597 A | 6/1994 | Sage, Jr. et al. |
| 5,320,598 A | 6/1994 | Haak et al. |
| 5,322,502 A | 6/1994 | Theeuwes et al. |
| 5,326,341 A | 7/1994 | Lew et al. |
| 5,344,394 A | 9/1994 | Gyory et al. |
| 5,354,324 A | 10/1994 | Gregory |
| 5,374,242 A | 12/1994 | Haak et al. |
| 5,380,271 A | 1/1995 | Gyory |
| 5,385,543 A | 1/1995 | Haak et al. |
| 5,387,189 A | 2/1995 | Gory et al. |
| 5,395,310 A | 3/1995 | Untereker et al. |
| 5,403,275 A | 4/1995 | Phipps |
| 5,405,317 A | 4/1995 | Myers et al. |
| 5,415,628 A | 5/1995 | Untereker et al. |
| 5,417,653 A | 5/1995 | Sahota et al. |
| 5,422,093 A | 6/1995 | Kennedy et al. |
| 5,423,739 A | 6/1995 | Phipps et al. |
| 5,423,803 A | 6/1995 | Tankovich et al. |
| 5,425,728 A | 6/1995 | Tankovich |
| 5,443,442 A | 8/1995 | Phipps et al. |
| 5,445,606 A | 8/1995 | Haak et al. |
| 5,445,609 A | 8/1995 | Lattin et al. |
| 5,445,611 A | 8/1995 | Eppstein et al. |
| 5,451,576 A | 9/1995 | Sessler et al. |
| 5,455,611 A | 10/1995 | Simon et al. |
| 5,458,569 A | 10/1995 | Kirk, III et al. |
| 5,464,387 A | 11/1995 | Haak et al. |
| 5,464,436 A | 11/1995 | Smith |
| 5,466,217 A | 11/1995 | Myers et al. |
| 5,474,528 A | 12/1995 | Meserol |
| 5,484,803 A | 1/1996 | Richter |
| 5,498,235 A | 3/1996 | Flower |
| 5,500,009 A | 3/1996 | Mendes et al. |
| 5,520,905 A | 5/1996 | Uhlmann et al. |
| 5,522,868 A | 6/1996 | Buckley et al. |
| 5,553,618 A | 9/1996 | Suzuki et al. |
| 5,586,981 A | 12/1996 | Hu |
| 5,601,526 A | 2/1997 | Chapelon et al. |
| 5,630,811 A | 5/1997 | Miller |
| 5,632,767 A | 5/1997 | Sinofsky |
| 5,633,275 A | 5/1997 | Mori et al. |
| 5,643,334 A | 7/1997 | Eckhouse et al. |
| 5,647,866 A | 7/1997 | Zaias et al. |
| 5,669,916 A | 9/1997 | Anderson |
| 5,671,314 A | 9/1997 | Gregory et al. |
| 5,709,654 A | 1/1998 | Klatz et al. |
| 5,713,845 A | 2/1998 | Tankovich |
| 5,725,522 A | 3/1998 | Sinofsky |
| 5,733,572 A | 3/1998 | Unger et al. |
| 5,735,844 A | 4/1998 | Anderson et al. |
| 5,736,563 A | 4/1998 | Richter |
| 5,752,948 A | 5/1998 | Tankovich et al. |
| 5,752,949 A | 5/1998 | Tankovich et al. |
| 5,763,235 A | 6/1998 | Watanabe |
| 5,776,174 A | 7/1998 | Van Tassel |
| 5,776,966 A | 7/1998 | North |
| 5,784,162 A | 7/1998 | Cabib et al. |
| 5,789,433 A | 8/1998 | Chan et al. |
| 5,798,349 A | 8/1998 | Levy et al. |
| 5,807,881 A | 9/1998 | Leong et al. |
| 5,817,089 A | 10/1998 | Tankovich et al. |
| 5,856,566 A | 1/1999 | Golub |
| 5,872,113 A | 2/1999 | Nestor, Jr. et al. |
| 5,876,426 A | 3/1999 | Kume et al. |
| 5,882,302 A | 3/1999 | Driscoll, Jr. et al. |
| 5,925,034 A | 7/1999 | Buckley et al. |
| 5,952,329 A | 9/1999 | Cincotta et al. |
| 5,955,490 A | 9/1999 | Kennedy et al. |
| 5,976,535 A | 11/1999 | Fritzberg et al. |
| 5,993,389 A | 11/1999 | Driscoll, Jr. et al. |
| 6,036,684 A | 3/2000 | Tankovich et al. |
| 6,050,990 A | 4/2000 | Tanovich et al. |
| 6,063,108 A | 5/2000 | Salansky et al. |
| 6,096,030 A | 8/2000 | Ortiz |
| 6,099,521 A | 8/2000 | Shadduck |
| 6,106,514 A | 8/2000 | O'Donnell, Jr. |
| 6,107,466 A | 8/2000 | Hasan et al. |
| 6,162,242 A | 12/2000 | Peyman |
| 6,165,170 A | 12/2000 | Wynne et al. |
| 6,168,590 B1 | 1/2001 | Neev |
| 6,180,402 B1 | 1/2001 | Granville et al. |
| 6,183,773 B1 | 2/2001 | Anderson |
| 6,231,593 B1 | 5/2001 | Meserol |
| 6,264,649 B1 | 7/2001 | Whitcroft et al. |
| 6,283,956 B1 | 9/2001 | McDaniel |
| 6,306,130 B1 | 10/2001 | Anderson et al. |

(56) References Cited

U.S. PATENT DOCUMENTS

| | | | |
|---|---|---|---|
| 6,358,242 | B1 | 3/2002 | Cecchetti |
| 6,358,272 | B1 | 3/2002 | Wilden |
| 6,365,145 | B1 | 4/2002 | Ben-Hur et al. |
| 6,380,254 | B2 | 4/2002 | Pearlstein et al. |
| 6,385,272 | B1 | 5/2002 | Takahashi |
| 6,408,212 | B1 | 6/2002 | Neev |
| 6,413,268 | B1 | 7/2002 | Hartman |
| 6,425,912 | B1 | 7/2002 | Knowlton |
| 6,428,532 | B1 | 8/2002 | Doukas et al. |
| 6,443,976 | B1 | 9/2002 | Flower et al. |
| 6,520,981 | B1 | 2/2003 | LaMuraglia |
| 6,529,543 | B1 | 3/2003 | Anderson et al. |
| 6,600,951 | B1 | 7/2003 | Anderson |
| 6,663,658 | B1 | 12/2003 | Kollias et al. |
| 6,743,211 | B1 | 6/2004 | Prausnitz et al. |
| 6,897,238 | B2 | 5/2005 | Anderson |
| 7,020,528 | B2 | 3/2006 | Neev |
| 7,066,929 | B1 | 6/2006 | Azar et al. |
| 7,220,778 | B2 | 5/2007 | Anderson et al. |
| 7,498,029 | B2 | 3/2009 | Hasan et al. |
| 7,659,301 | B2 | 2/2010 | Anderson et al. |
| 8,073,531 | B2 * | 12/2011 | Goldman et al. ............. 600/473 |
| 2001/0027206 | A1 | 10/2001 | Pearlstein et al. |
| 2001/0051742 | A1 | 12/2001 | Hasegawa et al. |
| 2002/0087205 | A1 | 7/2002 | Chen |
| 2002/0095067 | A1 | 7/2002 | Guenst et al. |
| 2002/0099094 | A1 | 7/2002 | Anderson |
| 2002/0127230 | A1 | 9/2002 | Chen |
| 2003/0083649 | A1 * | 5/2003 | Margaron et al. ................ 606/4 |
| 2003/0125388 | A1 | 7/2003 | Gander et al. |
| 2003/0212443 | A1 | 11/2003 | LaMuraglia |
| 2004/0006328 | A1 | 1/2004 | Anderson |
| 2004/0102822 | A1 | 5/2004 | Cohn |
| 2004/0259854 | A1 | 12/2004 | Anderson et al. |
| 2004/0259855 | A1 | 12/2004 | Anderson et al. |
| 2005/0014431 | A1 | 1/2005 | Carmody et al. |
| 2005/0045189 | A1 * | 3/2005 | Jay ................................ 128/898 |
| 2005/0143466 | A1 | 6/2005 | Anderson |
| 2006/0004347 | A1 | 1/2006 | Altshuler et al. |
| 2006/0269580 | A1 | 11/2006 | Cole et al. |
| 2007/0038270 | A1 | 2/2007 | Ferren et al. |
| 2007/0173913 | A1 | 7/2007 | Anderson et al. |
| 2007/0197884 | A1 * | 8/2007 | Bornstein ..................... 600/310 |
| 2007/0264288 | A1 | 11/2007 | Manstein |
| 2008/0051773 | A1 | 2/2008 | Ivanov et al. |
| 2009/0299268 | A1 | 12/2009 | Anderson |
| 2010/0098677 | A1 | 4/2010 | Anderson et al. |

FOREIGN PATENT DOCUMENTS

| | | |
|---|---|---|
| EP | 0 726 083 A3 | 12/1998 |
| FR | 2 764 813 A1 | 12/1998 |
| JP | 10-165410 | 6/1998 |
| WO | 89/07907 A1 | 9/1989 |
| WO | 94/06424 A1 | 3/1994 |
| WO | 95/07077 A1 | 3/1995 |
| WO | 96/09853 A1 | 4/1996 |
| WO | 96/14899 A1 | 5/1996 |
| WO | 96/39188 A1 | 12/1996 |
| WO | 96/41579 A1 | 12/1996 |
| WO | 97/00098 A1 | 1/1997 |
| WO | 98/07909 A2 | 2/1998 |
| WO | 98/30242 A2 | 7/1998 |
| WO | 98/33444 A1 | 8/1998 |
| WO | 98/52610 A1 | 11/1998 |
| WO | 98/53847 A1 | 12/1998 |
| WO | 00/40266 A2 | 7/2000 |
| WO | 00/41727 A1 | 7/2000 |
| WO | 01/35996 A2 | 5/2001 |
| WO | 01/35997 A2 | 5/2001 |
| WO | 01/55092 A2 | 8/2001 |
| WO | WO 03/017824 | 3/2003 |
| WO | 2005/120572 A1 | 12/2005 |
| WO | 2006/051269 A1 | 5/2006 |

OTHER PUBLICATIONS

[No Author] Guide for the Care and Use of Laboratory Animals. Institute of Laboratory Animal Resources, Commission on Life Sciences, National Research Council. National Academy Press, Washington, DC.1996.

[No Author] More about lasers. ShoreLaser Center. Retrieved Jul. 3, 2003 from http://www.shorelaser.com/AboutLasersDet.html. (8 Pages).

Adili, F., et al., "Local Delivery of Photosensitizing Drugs in Arteries: A Novel Approach to Photodynamic Therapy for the Prevention of Intimal Hyperplasia," SPIE 2395: 402-408 (1995).

Adili, F., et al., "Photodynamic Therapy with Local Photosensitizer Delivery Inhibits Experimental Intimal Hyperplasia," Lasers in Surg. Med., 23(5): 263-273 (1998).

Adili, E, et al., "Significance of Dosimetry in Photodynamic Therapy of Injured Arteries: Classification of Biological Responses," Photochem. Photobio., 70(4): 663-668 (1999).

Anderson, R.R., Optics of the skin. Clinical Photomedicine. Lim et al., eds., Ch. 2, 19-35, 1993, Marcel Dekker, New York, NY.

Apfel et al., Gauging the likelihood of cavitation from short-pulse, low-duty cycle diagnostic ultrasound. Ultrasound Med Biol. 1991;17(2):179-85.

Arakane et al. "Singlet Oxygen (1 delta g) Generation from Coproporphyrin in Propionibacterium acnes on Irradiation" Biochemical and Biophysical Research Communications, vol. 223(3), article 0937, pp. 578-582 (1996).

Barnett et al., The sensitivity of biological tissue to ultrasound. Ultrasound in Med & Biol. 1997;23(6):805-12.

Bissonnette et al., Current status of photodynamic therapy in dermatology. Dermatol Clin. Jul. 1997;15(3):507-19.

Bjorklund, G.C., Effects of focusing on third-order nonlinear processes in isotropic media. IEEE Journal of Quantum Electronics. Jun. 1975;11(6):287-96.

Brookner, et al. "Safety Analysis: Relative Risks of Ultraviolet Exposure from Fluorescence Spectroscopy and Colposcopy Are Comparable" Photochemistry and Photobiology, vol. 65, No. 6pgs. 1020-1025(1997).

Bryant, S.R., et al., "Vascular Remodeling in Response to Altered Blood Flow is Mediated by Fibroblast Growth Factor-2," Cir. Res., 84: 323-328 (1999).

Burke et al., The assessment of acne vulgaris—the Leeds technique. Br J Dermatol. Jul. 1984;111(1):83-92.

Camenzind, E., et al., "Use of Locally Delivered Conventional Drug Therapies," Semin. Interv. Cardiol., 1:67-76 (1996).

Canadian Office Action issued Sep. 11, 2007 for Application No. 2,360,202 (6 Pages).

Canadian Office Action issued Aug. 8, 2003 for Application No. 2,369,792 (2 Pages).

Canadian Office Action issued May 6, 2004 for Application No. 2,369,792 (4 Pages).

Canadian Office Action issued Jan. 3, 2006 for Application No. 2,422,865 (5 Pages).

Canadian Office Action issued Jan. 9, 2007 for Application No. 2,422,865 (6 Pages).

Canadian Office Action issued Dec. 14, 2010 for Application No. 2,422,865 (8 Pages).

Chernoff, W.G., Selective photothermolysis for hair removal. Retrieved Jul. 3, 2003 from http://lastertraining.com/med-13.htm. LaserTraining.com. Lasertrolysis of Naples. (10 Pages).

Clowes, A.W., "Pathologic Intimal Hyperplasia as a Response to Vascular Injury and Reconstruction," Vascular Surgery, 1: 285-295 (1995).

Coats, W. D. Jr., et al., "Tin Ethyl Etiopurpurin Significantly Inhibits Vascular Smooth Muscle Cell Proliferation in Vivo," Biochem. Cell Biol., 74(3): 325-332 (1996).

Coleman, M.D., et al., "Drug-Induced Methaemoglobinaemia," Pharmacoepidemiology, 14(6): 394-405 (Jun. 1996).

Davies, M.G., et al., "Pathobiology of Intimal Hyperplasia," British J. Of Surg., 81: 1254-1269 (1994).

(56) References Cited

OTHER PUBLICATIONS

Delius et al., Acoustic energy determines haemoglobin release from erythrocytes by extracorporeal shock waves in vitro. Ultrasound Med Biol. 1995;21(5):707-10.
Deyoung et al., "Gene Therapy for Restenosis. Are We Ready?," Circ. Res., 82: 306-313 (1998).
Dierickx, et al. "Photodynamic Therapy for Nevus Sebaceus with Topical Aminolevulinic Acid" Arch Dermatol, vol. 135 (6), pp. 637-640 (1999).
Divaris, D. et al., "Phototoxic Damage to Sebaceous Glands and Hair Follicles of Mice After Systemic Administration of 5-Aminolevulinic Acid Correlates With Localized Protoporphyrin IX Fluorescence," Am. J. Pathol. 136(4):891-897 (1990).
Diven et al., Dye-enhanced diode laser photothermal ablation of skin. J Am Acad Dermatol. Aug. 1996;35(2 Pt 1):211-5.
Dougherty et al., Photodynamic therapy. J Natl Cancer Inst. Jun. 17, 1998;90(12):889-905.
Dubbelman, T., et al., "Photodynamic Therapy: Membrane and Enzyme Photobiology," Photodynamic Therapy. Basic Principles and Clinical Applications, 37-46 (1992).
Dunn et al., Ultrasonic threshold dosages for the mammalian central nervous system. IEEE Trans Biomed Eng. Jul. 1971;18(4):253-6.
Eton, D., et al., "Photodynamic Therapy," Arch Surg., 130: 1098-1103 (1995).
European Examination Report issued Mar. 29, 2005 for Application No. 00926402.9 (6 Pages).
European Examination Report issued Oct. 11, 2007 for Application No. 00926402.9 (4 Pages).
European Search Report issued Dec. 9, 2004 for Application No. 01971365.0 (3 Pages).
European Examination Report issued Apr. 4, 2006 for Application No. 01971365.0 (4 Pages).
European extended search report, from corresponding EP 10003702.7, dated Nov. 8, 2010 (11 Pages).
European search report, from corresponding EP 10180457.3, dated Dec. 14, 2010 (11 Pages).
Evanko, S.P., et al. "Formation of Hyaluronan- and Versican-Rich Pericellular Matrix is Required for Proliferation and Migration of Vascular Smooth Muscle Cells," Aterioscler. Thromb. Vasc. Biol., 19: 1004-1013 (1999).
Evanko, S.P., et al., "Proteoglycan Distribution in Lesions of Atherosclerosis Depends on Lesion Severity, Structural Characteristics, and the Proximity of Platelet-Derived Growth Factor and Transforming Growth Factor-?," Amer. J. Path., 152(2): 533-546 (Feb. 1998).
Fatemi et al., Ultrasound-stimulated vibro-acoustic spectrography. Science. Apr. 3, 1998;280:82-84.
Fisher, A., et al., "Clinical and Preclinical Photodynamic Therapy," Lasers Surg. Med. , 17: 2-31 (1995).
Forrester, J., et al., "A Paradigm for Restenosis Based on Cell Biology: Clues for the Development of New Preventive Therapies," JACC, 17(3): 758-769 (Mar. 1, 1991).
Fowler, AJ, Investigation of two-beam selective photothermolysis. Mechanical Engineering Department, Univserity of Massachusetts Dartmouth and Center for Engineering in Medicine in Medicine, Massachusetts General Hospital, 1999 (2 Pages).
Gasparro et al., Rapid and sensitive analysis of 8-methoxypsoralen in plasma. J Invest Dermatol. Feb. 1988;90 (2):234-6.
Geary, R.L., et al., "Wound Healing: A Paradigm for Lumen Narrowing After Arterial Reconstruction," J. Vasc. Surg., 27(1): 96-108 (Jan. 1998).
Gfesser, et al. "Seasonal Variations in the Severity of Acne Vulgaris" International Journal of Dermatology, vol. 35, No. 2, pp. 116-117 (1996).
Gonschior, P., et. al., "Local Photodynamic Therapy Reduces Tissue Hyperplasia in an Experimental Restenosis Model," Photochem. Photobio., 64(5): 758-763 (1996).
Grant, W.E., et al., "Photodynamic Therapy of Normal Rat Arteries After Photosensitisation Using Disulphonated Aluminum Phthalocyanine and 5-Aminolaevulinic Acid," Br. J. Cancer., 70: 72-78 (1994).
Grant, W.E., et al., "The Effect of Photodynamic Therapy on the Mechanical Integrity of Normal Rabbit Carotid Arteries," Laryngoscope, 105: 867-871 (Aug. 1995).
Gregoriadis, G., ed., Liposome Technology. CRC Press, Boca Raton, FL, 1984, vols. 1-3. vol. 1-Ch. 1-4; 6-9; 11, vol. 2-Ch. 8, vol. 3-Ch. 1 and 8.
Griffiths et al., Topical therapy. Textbook of Dermatology. Ch. 75, pp. 3037-3046. Rook et al., eds, Blackwell Scientific, London, 1992.
Grinnell, F., "Fibroblasts, Myofibroblasts, and Wound Contraction," J. Cell Bio., 124(4): 401-404 (Feb. 1994).
Heckenkamp et al., Different effects of photodynamic therapy and ?-irradiation on vascular smooth muscle cells and matric implications for inhibiting restenosis. Arterioscler Thromb Vasc Biol. Sep. 1999;19:2154-61.
Heckenkamp, J., et al., "Local Photodynamic Action of Methylene Blue Favorably Modulates the Postinterventional Vascular Wound Healing Response," Journal of Vascular Surgery, 31(6): 1168-1177 (2000).
Henderson, B.W., et al., "How Does Photodynamic Therapy Work?," Photochem. Photobio., 55(1): 145-157 (1992).
Henderson, D.J. et al., "Versican Expression is Associated with Chamber Specification, Septation, and Valvulogenesis in the Developing Mouse Heart," Circ. Res., 83: 523-532 (1998).
Hilf, R., "Cellular Targets of Photodynamic Therapy as a Guide to Mechanisms," Photodynamic Therapy. Basic Principles and Clinical Applications, 47-54 (1992).
"Hongcharu et al., The Society for Investigavite Dermatology, Inc., ""Topical ALA-Photodynamic Therapy for the Treatment of Acne Vulgaris"", pp. 1-9, (2000)."
Hsiang, Y.N., et al., "Dosage and Timing of Photofrin for Photodynamic Therapy of Intimal Hyperplasia," Cardiovascular Surgery, 3(5): 489-494 (1995).
Hsiang, Y.N., et al., "Photodynamic Therapy for Atherosclerotic Stenoses in Yucatan Miniswine," JCC, 37(2): 148-152 (Apr. 1994).
Hsiang, Y.N., et al., "Preventing Intimal Hyperplasia with Photodynamic Therapy Using an Intravascular Probe," Ann. Vasc. Surg., 9(1): 80-86 (1995).
Hsiang, Y.N., et al., "Preventing Restenosis in Atherosclerotic Miniswine with Photodynamic Therapy," SPIE, 2395: 384-389 (1995).
Huehns, T.Y., et al., "Adventia as a Target for Intravascular Local Drug Delivery," Heart, 75: 537-538 (1996).
International Search Report mailed Jul. 12, 2000 for Application No. PCT/US99/29974 (10 Pages).
Written Opinion mailed Nov. 3, 2000 for Application No. PCT/US99/29974 (7 Pages).
International Preliminary Examination Report issued Apr. 4, 2001 for Application No. PCT/US99/29974 (14 Pages).
International Search Report mailed Aug. 7, 2000 for Application No. PCT/US00/11248 (7 Pages).
Written Opinion mailed Feb. 12, 2001 for Application No. PCT/US00/11248 (4 Pages).
International Preliminary Examination Report mailed Jul. 13, 2001 for Application No. PCT/US00/11248 (5 Pages).
International Search Report mailed Sep. 28, 2001 for Application No. PCT/US00/27140 (9 Pages).
Written Opinion mailed Dec. 11, 2001 for Application No. PCT/US00/27140 (8 Pages).
International Preliminary Examination Report mailed Feb. 13, 2002 for Application No. PCT/US00/27140 (9 Pages).
International Search Report mailed Dec. 31, 2001 for Application No. PCT/US2001/041691 (4 Pages).
Written Opinion mailed Aug. 30, 2002 for Application No. PCT/US2001/041691 (6 Pages).
International Preliminary Examination Report mailed Nov. 20, 2002 for Application No. PCT/US2001/041691 (6 Pages).
International Search Report mailed Sep. 22, 2004 for Application No. PCT/US2004/011585 (4 Pages).
International Preliminary Report on Patentability mailed Nov. 3, 2005 for Application No. PCT/US2004/011585 (5 Pages).
International Search Report and Written Opinion mailed Apr. 6, 2005 for Application No. PCT/US2004/011624 (8 Pages).

(56) References Cited

OTHER PUBLICATIONS

International Preliminary Report on Patentability mailed Nov. 3, 2005 for Application No. PCT/US2004/011624 (5 Pages).
Ito et al., Experience in photodynamic therapy using ?-aminolevulinic acid on acne vulgaris. The Journal of Japan Society for Laser Surgery and Medicine. Jun. 28, 2000;21(2):168. (Japanese Language Reference).
Ito, K., et al., "Multiple Forms of Mouse PG-M, a Large Chondroitin Sulfate Proteoglycan Generated by Alternative Splicing," J. Bio. Chem., 270(2): 958-965 (1995).
Itoh et al, "Photodynamic therapy for acne vulgaris with topical 5-aminolevulinic acid," Arch of Derm 136(9): 1093-95 (2000).
Itoh et al, "Photodynamic therapy of acne vulgaris with topical delta-aminolaevulinic acid and incoherent light on Japanese patients," British J Derm. 144(3):575-79 (2001).
Jacques et al., Modeling optical and thermal distributions in tissue during laser irradiation. Lasers Surg Med. 1987;6 (6):494-503.
Jacques, S.L., Light distributions from point, line and plane sources for photochemical reactions and fluorescence in turbid biological tissues. Photochem Photobiol. Jan. 1998;67(1):23-32.
Japanese Office Action issued Sep. 27, 2011 for Application No. 2002-518935.
Jarry et al., Extinction measurements in diffusing mammalian tissue with heterodyne detection and a titanium:sapphire laser. Appl Opt. Apr. 20, 1995;34(12):2045-54. doi: 10.1364/AO.34.002045.
Jenkins, MP., et al., "Intra-Arterial Photodynamic Therapy Using 5-ALA in a Swine Model," Eur. J. Vasc. Endovasc. Surg., 16: 284-291 (1998).
Joe et al., Spatial confinement of 5-aminolevulinic acid-based photodynamic therapy. Wellman Laboratories of Photomedicine, Massachusetts General Hospital, Department of Dermatology, Harvard Medical School, Boston, MA. Presentation. 2002-2003 (1 Pages).
Kagan, S.A., et al., "Mediators of Restenosis," Surg. Clinics of N. Amer., 78(3): 481-501 (Jun. 1998).
Kalka et al., Phtodynamic therapy in dermatology. Journal of the American Academy of Dermatology. Mar. 2000;42 (3):389-413.
Kaufman et al., Endovascular repair of abdominal aortic aneurysms: current status and future directions. American J Roentgenology. Aug. 2000;175:289-302.
Kim et al., Ultrasound-mediated transfection of mammalian cells. Human Gene Therapy. Jul. 10, 1996;7:1339-1346.
Kishimoto, J., et al., "Cellular Localization of Putative Odorant Receptor mRNAs in Olfactory and Chemosensory Neurons: a Non-Radioactive in Situ Hybridization Study," Mol. Brain Res., 23: 33-39 (1994).
Kjeldstad et al. "Changes in Polyphosphate Composition and Localization in Propionibacterium Acnes After Near-Ultraviolet Irradiation" Can J. Microbiol, vol. 37, pp. 562-567 (1991).
Kloek et al., Photochemistry and Photobiology, "Prodrugs of 5-Aminolevulinic Acid for Photodynamic therapy", pp. 994-1000,64(6), (1996).
Kollias, et al. "Endogenous Skin Fluorescence Includes Bands that may Serve as quantitative Markers of Aging and Photoaging" The Journal of Investigative Dermatology, vol. 111, No. 5, pp. 776-780 (1998).
König, et al. "Photodynamic Induced Inactivation of Propionibacterium Acnes Using the Photosensitizer Methylene Blue and Red Light" Dermatologische Monatsschrift, vol. 178, pp. 297-300 (1992).
König, et al. "Photodynamische Aktivitat von Methylenblau" Akt. Dermatol, vol. 19, pp. 195-198 (1993). [German] Abstract Only.
König, et al. "Photodynamically Inactivation of Propionibacterium Acnes" SPIE, vol. 3247 pp. 106-110 (1998).
Kuhn et al., Acneiform papules on the neck. Arch Dermatol. 1995;131(3):341-2.
Kypreos, K.E., "Basic Fibroblast Growth Factor-Induced Decrease in Type I Collagen Gene Transcription is Mediated by B-Myb1," Cell Growth & Differentiation, 9: 723-730 (Sep. 1998).

Lambert, C.R., et al., "Local Drug Delivery Catheters: Functional Comparison of Porous and Microporous Designs," Coronary Artery Disease. 4(5):469-475 (1993).
Lambert, C.R., et al., "Microporous Infusion Catheter," Semin. Intervent. Cardiol., 1:30-31 (1996).
Lammer J., Laser angioplasty of peripheral arteries: an epilogue? Cardiovasc Intervent Radiol. Jan.-Feb. 1995;18 (1):1-8.
Lamuraglia, G.M., et al., "Chloroaluminum Sulfonated Phthalocyanine Partitioning in Normal and Intimal Hyperplastic Artery in the Rat," Am. J. Pathol., 142(6): 1898-1905 (Jun. 1993).
Lamuraglia, G.M., et al., "Photodynamic Therapy Inactivates Extracellular Matrix-Basic Fibroblast Growth Factor: Insights to its Effect on the Vascular Wall," J. Vasc. Surg., 26(2): 294-301 (Aug. 1997).
Lamuraglia, G.M., et al., "Photodynamic Therapy Inhibition of Experimental Intimal Hyperplasia: Acute and Chronic Effects," J. Vasc. Surg., 19(2): 321-331 (Feb. 1994).
Larsson, L.I., et al. " Optimization of Non-Radioactive In Situ Hybridization: Image Analysis of Varying Pretreatment, Hybridization and Probe Labeling Conditions," Histochem., 93: 347-354 (1990).
Lassus et al., [Treatment of acne with selective UV-phototherapy (SUP): an open trial]. Dermatol Monatsschr. Jun. 1983;169(6):376-9. (German Language Reference) (English Abstract Only).
Laurent, G.J., "Dynamic State of Collagen: Pathways of Collagen Degradation In Vivo and Their Possible Role in Regulation of Collagen Mass," Amer. J. Physio., 252: C1-C9 (1987).
Lee et al., Stress-wave-induced membrane permeation of red blood cells is facilitated by aquaporins. Ultrasound Med Biol. 1997;23(7):1089-94.
Levine et al., Effects on hyperpolarizabilities of molecular interactions in associating liquid mixtures. J Chem Phys. 1976;65(6):2429-38.
Li., S.W., et al "The Complete cDNA Coding Sequence for the Mouse Pro ?1(I) Chain of Type I Procollagen," Matrix Bio., 14: 593-595 (1994).
Lide, D.R., ed., CRC Handbook of Chemistry and Physics. 79th Edition. 1998. CRC Press, New York, NY., Ch. 9, 10 and 14.
Lieb et al., Topical delivery enhancement with multilamellar liposomes into pilosebaceous units: I. In vitro evaluation using fluorescent techniques with the hamster ear model. J Invest Dermatol. Jul. 1992;99(1):108-13.
Liu et al., Non-invasive assessment and control of ultrasound-mediated membrane permeabilization. Pharm Res. Jun. 1998;15(6):918-24.
Lloyd et al., Selective photothermolysis of the sebaceous glands for acne treatment. Lasers in Surgery and Medicine. 2002;31:115-20.
Macsai et al., Acne rosacea. Eye and Skin Disease. Mannis et al, eds, Ch. 41, pp. 335-341, Lippincott-Raven Publishers, New York, NY, 1996.
Matsuura, R. et al., "Deposition of PG-M/Veriscan is a Major Cause of Human Coronary Restenosis After Percutaneous Transluminal Coronary Angioplasty," J. Path., 180: 311-316 (1996).
Meffert et al., [Phototherapy of acne vulgaris with the UVA irradiation instrument TBG 400. Dermatol Monatsschr]. 1986;172(2):105-6. (German Language Reference).
Meffert et al., [Phototherapy of acne vulgaris with the "TuR" UV 10 body section irradiation unit]. Dermatol Monatsschr. 1986;172(1):9-13. (German Language Reference) (English Abstract Only).
Meffert et al., Treatment of acne vulgaris with visible light. Dermatol Monatsschr. 1987;173(11):678-9.
Meffert et al., [Therapy of acne with visible light. Decreased irradiation time by using a blue-light high-energy lamp]. Dermatol Monatsschr. 1990;176(10):597-603. (German Language Reference) (English Abstract Only).
Menovsky et al., Laser(-assisted) nerve repair. A review. Neurosurg Rev. 1995;18(4):225-35.
Meyer, B.J., et al., "Local Delivery of r-Hirudin by a Double-Balloon Perfusion Catheter Prevents Mural Thrombosis and Minimizes Platelet Deposition After Angioplasty," Circulation, 90(5): 2474-2480 (Nov. 1994).
"Michaëlsson et al., Effects of oral zinc and vitamin A in acne. Arch Dermatol. Jan. 1977;113(1):31-6.".

(56) References Cited

OTHER PUBLICATIONS

Miller et al., Ultrasound contrast agents nucleate interial cavitation in vitro. Ultrasound in Med & Biol. 1995;21 (8):1059-1065.
Miller et al., A review of in vitro bioeffects of inertial ultrasonic cavitation from a mechanistic perspective. Ultrasound in Med & Biol. 1996;22(9):1131-1154.
Mills et al., Enhancement of comedogenic substances by ultraviolet radiation. Br J Dermatol. Feb. 1978;98(2):145-50.
Mills, et al. "Ultraviolet Phototherapy and Photochemotherapy of Acne Vulgaris" Arch Dermatol, vol. 114, pp. 221-223 (1978).
Moan et al., The biophysical foundations of photodynamic therapy. Endoscopy. May 1998;30(4):387-91.
Morales, T.G., et al., "Methylene Blue Staining for Intestinal Metaplasia of the Gastric Cardia with Follow-up for Dysplasia," Gastrointest. Endosc., 48(1): 26-31 (1998).
Morgan et al., Free radical production by high energy shock waves— comparison with ionizing irradiation. The Journal of Urology. 1988;139:186-9.
Morton et al., The role of cavitation in the interaction of ultrasound with V79 Chinese hamster cells in vitro. Br J Cancer Suppl. Mar. 1982;45:147-50.
Mutzhas, et al. "A New Apparatus with High Radiation Energy Between 320-460 nm: Physical Description and Dermatological Applications" The Journal of Investigative Dermatology, vol. 76 pp. 42-47 (1981).
Naess et al. "In Vivo and in Vitro Effects of Doxycycline on Leucocyte Membrane Receptors" Clin Exp Immunol, vol. 62, pp. 310-314 (1985).
Nyamekye, I., et al., "Inhibition of Intimal Hyperplasia in Balloon Injured Arteries with Adjunctive Phthalocyanine Sensitised Photodynamic Therapy," Eur. J. Vasc. Endovasc. Surg., 11: 19-28 (1996).
Nyamekye, I., et al., "Photodynamic Therapy of Normal and Balloon-Injured Rat Carotid Arteries Using 5-Amino-Levulinic Acid" Circulation, 91(2): 417-425 (Jan. 15, 1995).
Ophir et al., Contrast agents in diagnostic ultrasound. Ultrasound Med Biol. 1989;15(4):319-33.
Orth, et al., "Methylene Blue Mediated Photodynamic Therapy in Experimental Colorectal Tumors in Mice," Journal of Photochemistry and Photobiology B: Biology, 57(2/3): 186-192 (2000).
Ortu, P., et al., "Photodynamic Therapy of Arteries. A Novel Approach for Treatment of Experimental Intimal Hyperplasia," Circulation, 85(3): 1189-1196 (Mar. 1992).
Ostro, M.J., Liposomes. Scientific American. Jan. 1987;256:102-111.
Overhaus et al., Photodynamic therapy generates a matrix barrier to invasive vascular cell migration. Circ. Res. Feb. 18, 2000;86:334-40.
Parrish, J.A, New concepts in therapeutic photomedicine: photochemistry, optical targeting and the therapeutic window. J Invest Dermatol. Jul. 1981;77(1):45-50.
Nadeau et al., In vivo measurement of 5-aminolaevulinic acid-induced protoporphyrin IX photobleaching: a comparison of red and blue light of various intensities. Photodermatol Photoimmunol Photomed. Aug. 2004;20(4):170-4.
Pass, H.I., "Photodynamic Therapy in Oncology: Mechanisms and Clinical Use," J. Natl. Cancer Inst., 85(6): 443-456 (Mar. 17, 1993).
Payne et al., Comparison of pulsed CO2 laser ablation at 10.6 microm and 9.5 microm. Lasers Surg Med. 1998;23 (1):1-6.
Peng et al., Build-up of esterfied aminolevulinic-acid-derivative-induced porphyrin fluorescence in normal mouse skin. Journal of Photochemistry and Photobiology B: Biology. 1996;34:95-6.
Peng et al., 5-Aminolevulinic acid-based photodynamic therapy: principles and experimental research. Photochem Photobiol. Feb. 1997;65(2):235-51.
Peng et al., 5-Aminolevulinic acid-based photodynamic therapy. Clinical research and future challenges. Cancer. Jun. 15, 1997;79(12):2282-308.
Pento et al., Drugs of the Future, "Delta-aminolevulinic acid. Photodynamic therapy, antineoplastic, agent for actinic keratoses, antiacne", pp. 11-17, 22(1) (1997).

Phillips, et al. "Recent Advances in Dermatology" The New England Journal of Medicine, vol. 326, No. 3, pp. 167-178 (1992).
Reidy, M., et al., "Factors Controlling the Development of Arterial Lesions After Injury," Circulation, 86(6): Supplement III: III-43-III-46 (Dec. 1992).
Rhodes et al., Iontophoretic delivery of ALA provides a quantitative model for ALA pharmacokinetics and PpIX phototoxicity in human skin. J Invest Dermatol. 1997;108:87-91.
Rockson, R.G., "Photoangioplasty of Human Atherosclerosis Using Antrin Photosensitizer," [Abstract] Photochem. Photobio., 67:79S (1998).
Rogers, C., et al., "Balloon-Artery Interactions During Stent Placement. A Finite Element Analysis Approach to Pressure, Compliance, and Stent Design as Contributors to Vascular Injury," Circ. Res., 84: 378-383 (1999).
Rück, A., et al., "Nonlinear Dynamics of Intracellular Methylene Blue During Light Activation of Cell Cultures," Photochem. Photobiol., 66(6):837-841 (1997).
Schmidt-Erfurth, U., et al., "In Vivo Uptake of Liposomal Benzoporphin Derivative and Photothrombosis in Experimental Corneal Neovascularization," Lasers Surg. Med., 17: 178-188 (1995).
Schönherr, E., et al., "Effects of Platelet-derived Growth Factor and Transforming Growth Factor-?1 on the Synthesis of a Large Versican-like Chondroitin Sulfate Proteoglycan by Arterial Smooth Muscle Cells," J. Bio. Chem., 266(26): 17640-17647 (1991).
Schwartz, R.S., et al., Artery size, neointima, and remodeling: Time for some standards. JACC, 32(7): 2087-2094 (Dec. 1998).
Schwartz, S., et al., "The Intima. Soil for Atherosclerosis and Restenosis," Circ. Res., 77(3): 445-465 (Sep. 1995).
Sharman, W. et al., Photodynamic therapeutics: basic principles and clinical applications. Drug Discov Today. Nov. 1999;4(11):507-517.
Shi, Y., et al., "Adventitial Remodeling After Coronary Arterial Injury," Circulation, 93:340-348 (1996).
Shi, Y. et al., "Adventitial Myofibroblasts Contribute to Neointimal Formation in Injured Porcine Coronary Arteries," Circulation, 94(7): 1655-1664 (Oct. 1, 1996).
Shi, Y., et al., "Origin of Extracellular Matrix Synthesis During Coronary Repair," Circulation, 95(4): 997-1006 (Feb. 18, 1997).
Shulman, D.G., "DUSA Pharmaceuticals Reports Encouraging Results in Phase 1/11 Acne Clinical Trial," DUSA Pharmaceuticals Inc., Mississauga (Oct. 7, 1996). 1 page.
Sigurdsson et al. "Phototherapy of Acne Vulgaris with Visible Light" Dermatology, vol. 194(3), pp. 256-260 (1997).
Sobeh, M.S., et al., "Induction or Prevention of Intimal Hyperplasia by Photodynamic Therapy in the Porcine Model," SPIE, 2395: 390-395 (1995).
Sommer et al., Transient cavitation in tissues during ultrasonically induced hyperthermia. Med Phys. Jan./Feb. 1982;9(1):1-3.
Stables, G.I., Photodynamic therapy in dermatology. Journal of Dermatological Treatment. 1999;10:213-219.
Statius Van EPS, R.G., et al., "Photodynamic Therapy Inactivates Cell-Associated Basic Fibroblast Growth Factor: a Silent Way of Vascular Smooth Muscle Cell Eradication," Cardiovasc. Res., 35: 334-340 (1997).
Statius Van EPS, R.G., et al., "Photodynamic Therapy Inhibits Transforming Growth Factor ? Activity Associated with Vascular Smooth Muscle Cell Injury," J. Vasc. Surg., 25(6): 1044-1053 (Jun. 1997).
Statius Van EPS, R.G., et al., "Photodynamic Therapy Inhibits the Injury-Induced Fibrotic Response of Vascular Smooth Muscle Cells," Eur. J. Vasc. Endovasc. Surg., 18: 417-423 (Nov. 1999).
Statius Van EPS, R.G., et al., "Photodynamic Therapy of Extracellular Matrix Stimulates Endothelial Cell Growth by Inactivation of Matrix-Associated Transforming Growth Factor-?," Lab. Invest., 76(2): 257-266 (1997).
Suhr et al., Cavitation-generated free radicals during shock wave exposure: investigations with cell-free solutions and suspended cells. Ultrasound in Med & Biol. 1991;17(8):761-8.
Suslick, K.S., ed., Ultrasound:Its Chemical, Physical and Biological Effects. Ch. 1-3 and 7-8, VCH Pub, New York, NY, 1988.
Tankovich et al., Laser doppler spectroscopy method in researches of blood hydrodynamics. Journal de Physique. Dec. 1987;48(C7):287-93.

(56) References Cited

OTHER PUBLICATIONS

Tavakkoli et al., A piezocomposite shock wave generator with electronic focusing capability: application for producing cavitation-induced lesions in rabbit liver. Ultrasound in Med & Biol. 1997;23(1):107-15.
Teirstein, P.S. et al., "Two-Year Follow-up After Catheter-Based Radiotherapy to Inhibit Coronary Restenosis,". Circulation, 99: 243-247 (Jan. 19, 1999).
Topaz, O., Plaque removal and thrombus dissolution with the photoacoustic energy of pulsed-wave lasers-biotissue interactions and their clinical manifestations. Cardiology. Sep.-Oct. 1996;87(5):384-91.
Tsilimbaris, M.K., et al., "Pthalocyanine Mediated Photodynamic Thrombosis of Experimental Corneal Neovascularization: Effect of Phthalocyanine Dose and Irradiation Onset Time on Vascular Occlusion Rate," Lasers Surg. Med., 15: 19-31 (1994).
Umemura et al., In vitro and in vivo enhancement of sonodynamically active cavitation by second-harmonic superimposition. J Acoust Soc Am. Jan. 1997;101(1):569-577.
van Leeuwen et al., Pulsed laser ablation of soft tissue. Optical-Thermal Response of Laser-Irradiated Tissue. Welch et al., eds., Ch. 21, pp. 709-721, Plenum Press, New York, NY, 1995.
Vincent, et al., "Effects of Benzoporphyrin Derivative Monoacid on Balloon Injured Arteries in a Swine Model of Restenosis," SPIE 2671: 72-77 (1996).
Vivino et al., Stable cavitation at low ultrasonic intensities induces cell death and inhibits 3H-TdR incorporation by co-na-stimulated murine lymphocites in vitro. Ultrasound in Med & Biol. 1985;11(5):751-9.
Wainwright, M., Non-porphyrin photosensitizers in biomedicine. Chem Soc Rev. 1996;32:351-359.
Waksman, R., et al., " Effect of Intravascular Irradiation on Cell Proliferation, Apoptosis, and Vascular Remodeling After Balloon Overstretch Injury of Porcine Coronary Arteries," Circulation, 96(6): 1944-1952 (Sep. 16, 1997).
Wight, T.N., et al., "Selective Deposits of Versican in the Extracellular Matrix of Restenotic Lesions from Human Peripheral Arteries," Amer. J. Path., 151(4): 963-973 (Oct. 1997).
Wilkin "Rosacea—Pathophysiology and Treatment" Arch Dermatol, vol. 130, pp. 359-362 (1994).
Yamanouchi et al., Tunable vacuum ultraviolet laser spectroscopy: excited state dynamics of jet-cooled molecules and van der Waals complexes. J Phys B: At Mol Opt Phys. 1995;28(2):133-65.
Yoon et al., Development and application of three-dimensional light distribution model for laser irradiated tissue. IEEE Journal of Quantrum Electronics. Oct. 1987;23(10):1721-33.
Zaplavnova et al.,[Use of lasers in the treatment of diseases of the cervix uteri and vulva]. Vopr Onkol. 1990;36 (12):1497-500. (Russian Language Article) (English Abstract Only).
Anderson, R.R., Experimental data filed by Applicant with letter of Aug. 5, 2013 from Nils Braun and Alexander Ortlieb of Maiwald Patentanwalts GmbH. 23 pages. Document D13.
Anderson et al., Selective photothermolysis: precise microsurgery by selective absorption of pulsed radiation. Science. Apr. 29, 1983;220(4596):524-7.
Cenens et al., Visible spectroscopy of methylene blue on hectorite, laponite B, and barasym in aqueous suspension. Clays and Clay Minerals. 1988, vol. 36, pp. 214-224.
Dalziel et al., The effects of isotretinoin on follicular and sebaceous gland differentiation. Br J Dermatol. Sep. 1987;117 (3):317-23.
Decision of the Board of Appeals for European Application No. 99968490.5 issued May 2, 2014 (23 pages).
Gomez, EC, Actions of isotretinoin and etretinate on the pilosebaceous unit. J Am Acad Dermatol. Apr. 1982;6(4 Pt 2 Suppl):746-50.
Lademann et al., Nanoparticles—an efficient carrier for drug delivery into the hair follicles. Eur J Pharm Biopharm. May 2007;66(2):159-64. Epub 2006 Nov 1.
Plewig et al., eds., The miraculous sebum suppression of isotretinoin. Acne and Rosacea. 2nd, Completely Revised and Enlarged Edition. Springer Verlag, New York, 1993, pp. 646-647.
Ross, E.V., Declaration of E.V. Ross, Jr., MD, dated Nov. 19, 2013, 8 pages (includes vita of Dr. Ross).

Saurat, JH, Side effects of systemic retinoids and their clinical management. J Am Acad Dermatol. Dec. 1992;27(6 Pt 2):S23-8.
U.S. Appl. No. 09/225,026, filed Jan. 4, 1999, Targeting of Sebaceous Follicles As a Treatment of Sebaceous Gland Disorders.
U.S. Appl. No. 09/460,860, filed Dec. 14, 1999, Selective Tissue Targeting by Difference Frequency of Two Wavelengths.
U.S. Appl. No. 09/464,137, filed Dec. 16, 1999, Targeting of Sebaceous Follicles as a Treatment of Sebaceous Gland Disorders.
U.S. Appl. No. 09/559,139, filed Apr. 27, 2000, Phototherapy Method for Treatment of Acne.
U.S. Appl. No. 09/678,174, filed Dec. 2, 2000, Significance of Dosimetry in Photodynamic Therapy of Injured Arteries.
U.S. Appl. No. 09/929,384, filed Aug. 14, 2001, Topical Aminolevulinic Acid-Photodynamic Therapy for the Treatment of Acne Vulgaris.
U.S. Appl. No. 10/314,590, filed Dec. 9, 2002, Significance of Dosimetry in Photodynamic Therapy of Injured Arteries.
U.S. Appl. No. 10/612,599, filed Jul. 2, 2003, Targeting of Sebaceous Follicles As a Treatment of Sebaceous Gland Disorders.
U.S. Appl. No. 10/709,121, filed Apr. 14, 2004, Methods and Devices for Epithelial Protection During Photodynamic Therapy.
U.S. Appl. No. 10/709,122, filed Apr. 14, 2004, Methods and Devices for Epithelial Protection During Photodynamic Therapy.
U.S. Appl. No. 10/970,922, filed Oct. 20, 2004, Topical Aminolevulinic Acid-Photodynamic Therapy for the Treatment of Acne Vulgaris.
U.S. Appl. No. 12/535,937, filed Aug. 5, 2009, Topical Aminolevulinic Acid-Photodynamic Therapy for the Treatment of Acne Vulgaris.
U.S. Appl. No. 13/566,442, filed Aug. 3, 2012, Topical Aminolevulinic Acid-Photodynamic Therapy for the Treatment of Acne Vulgaris.
Anderson, R.R. et al., J Invest Dermatol 1981;77;13-19.
Chen et al., "Oxygen Effect of Photodynamic Therapy" (abstract only), Database CAPLUS AN 1997:415867, Proceedings of SPIE-Intl. Soc. Optical Eng. 2972:80-87 (1997).
European Search Report, from related EP 08781098.2 Issued Jul. 7, 2010.
Fritsch, C. et al., "Photodynamic Therapy in Dermatology," Arch. Dermatol. 134:207-14 (1998).
Gonzalez et al., "Treatment of Dunning R3327-AT Rat Prostate Tumors . . . " (abstract only), Database CAPLUS AN 1986:438348, Cancer Research 46(6):2585-62 (1986).
Hongcharu et al, "Topical ALA-photodynamic therapy for the treatment of acne vulgaris," J Invest Dermatol, 115, 183-192 (2000).
International Search Report, from PCT/US08/68593, mailed Sep. 22, 2006.
Kennedy et al., "Photodynamic therapy with endogenous protoporphyrin IX: basic principles and present clinical experience," J Photochem Photobiol B (1990), 6:143-148.
Kennedy et al., "Endogenous protoporphyrin IX, a clinically useful photosensitizer for photodynamic therapy," J Photochem Photobiol B: Biol (1992), 14:275-92.
Kennedy et al., "Photodynamic therapy (PDT) and photodiagnosis (PD) using endogenous photosensitization induced by 5-aminolevulinic acid (ALA): mechanisms and clinical results," J Clin Laser Med Surg (1996), 14:289-304.
Khan, MH et al., "Intradermally focused infrared laser pulses: thermal effects at defined tissue depths," Lasers Surg. Med. 9999:1-11 (2005).
Manstein, D. et al., "Fractional photothermolysis: A new concept for cutaneous remodeling using microscopic patterns of thermal injury," Lasers Surg. Med. 34:426-38 (2004).
Paul et al., "Alkyl-Substituted Magnesium Phthalocyanine . . . " (abstract only), Database CAPLUS AN 2003:10752 J. Porphyrins & Phthalocyanines 6(5):340-46 (2002).
Sperduto et al., "Photodynamic therapy for chest wall recurrence in breast cancer," Int J Radiat Oncol Biol Phys 21:441-46 (1991).
Walther et al., "Phase I trial of photodynamic therapy in the treatment of recurrent superficial transitional cell carcimoma of the bladder," Urology 50:199-206 (1997).
Wyld et al., "The Influence of Hypoxia and pH on Amnioaevulinic Acid . . . " (abstract only), Database CAPLUS AN 1998:384288, British J. Cancer 77(10):1621-27 (1998).

* cited by examiner

METHOD AND APPARATUS FOR OPTICAL INHIBITION OF PHOTODYNAMIC THERAPY

CROSS REFERENCE TO RELATED APPLICATIONS

This application is a continuation-in-part of PCT International Application No. PCT/U.S.08/068,593 filed on Jun. 27, 2008, which claims priority to U.S. Provisional Application Ser. No. 60/946,536, filed on Jun. 27, 2007, the disclosures of which are incorporated herein by reference in their entireties.

FIELD OF THE INVENTION

The present invention relates to methods and apparatus for protecting non-target tissue (e.g., epithelial tissue) during photodynamic therapy using optical inhibition.

BACKGROUND

Photodynamic therapy ("PDT") generally involves a local or systemic application of a light-absorbing photosensitive agent, or photosensitizer, which may accumulate selectively in certain target tissues. Upon irradiation with electromagnetic radiation, such as visible light of an appropriate wavelength, reactive oxygen species (e.g., singlet oxygen and/or free radicals) may be produced in cells or other tissue containing the photosensitizer, which promotes cell damage or death. The oxidative damage from these reactive intermediates is generally localized to the cells or structures at which the photosensitizer is present. PDT treatments therefore may be capable of 'targeting' specific cells and lesions, for example, if the photosensitizer is present in significant quantity only at desired target sites and/or light activation is performed only at such target sites.

A precursor photosensitizer, such as aminolevulinic acid ("ALA") or a derivative of ALA such as an ALA-ester, which converts into a photosensitizer (e.g., a porphyrin) when it metabolizes, can also be used in PDT treatments. ALA is an FDA-approved topical PDT agent. ALA is generally the first committed precursor of heme synthesis, and occurs naturally in mammalian cells. When supplied in excess, ALA can overdrive the heme synthesis pathway until intracellular iron stores are depleted, after which photosensitizing porphyrins (e.g., protoporphyrin IX) may accumulate in tissues as originally described, e.g., in Kennedy et al., "Photodynamic therapy with endogenous protoporphyrin IX: basic principles and present clinical experience," J Photochem Photobiol B (1990), 6:143-148; Kennedy et al., "Endogenous protoporphyrin IX, a clinically useful photosensitizer for photodynamic therapy," J Photochem Photobiol B: Biol (1992), 14:275-92; and Kennedy et al., "Photodynamic therapy (PDT) and photodiagnosis (PD) using endogenous photosensitization induced by 5-aminolevulinic acid (ALA): mechanisms and clinical results," J Clin Laser Med Surg (1996), 14:289-304.

PDT has been used to treat various medical conditions, including infectious diseases, malignant diseases (such as skin cancers, lymphomas, etc), premalignant conditions (as actinic keratosis), viral warts, hair removal, etc. in many different medical fields, including dermatology, opthalmology, oncology, and others.

For example, ALA-PDT is a potent, long-lasting treatment for severe and scarring acne vulgaris, a common skin disease caused by abnormalities of sebaceous follicles in skin that can lead to permanent scars and disfigurement. PDT is observed to have about the same potency as oral isotretinoin (Accutane®), a very effective treatment. However, isotretinoin, which suppresses sebaceous (oil) gland function in the skin, is dangerous because it may cause birth defects if a woman becomes pregnant during or after taking the drug. PDT treatment can pose a far lower risk than application of oral isotretinoin, is less expensive and has fewer side effects, does not require blood tests, can be used in women of childbearing potential, and can efficiently control severe acne. A course of 1-4 PDT treatments given over 3 months typically inhibits acne for a period varying between several months to permanently. Retreatment can be performed as needed. However, PDT treatment of acne vulgaris using ALA and/or methyl-ALA can have undesirable side effects such as epidermal photosensitization, which causes pain during light exposure, sunburn-like reactions, and/or post-treatment pigmentation as described, e.g., in Hongcharu et al, "Topical ALA-photodynamic therapy for the treatment of acne vulgaris," J Invest Dermatol, 115, 183-192 (2000).

Although PDT techniques using a photosensitizer or precursor photosensitizer can be effective for certain applications, it is often difficult to control application to the treatment area. For example, the photosensitizer or precursor photosensitizer can be absorbed and/or accumulate in healthy tissues as well as the target tissue. In hair removal, for example, a photosensitizer or precursor photosensitizer that is applied to the skin topically may be absorbed by both the epidermal and dermal layers of the skin. As a result, application of light can cause phototoxicity to the epidermis, which can lead to long-lasting hyperpigmentation or epidermal necrosis. In general, PDT treatments of subepithelial tissue using topically-applied photosensitizers often leads to unwanted damage to the epithelial tissue.

Thermal or chemical inhibition of photosensitizer formation in epithelial tissue from precursors can be used to reduce unwanted damage to such tissue. However, it may be difficult to accurately control the formation and accumulation of photosensitizers in particular tissues and/or tissue layers using thermal or chemical techniques. Also, such techniques can further interfere with the PDT process when using photosensitizers such as ALA.

Accordingly, there is a need for an improved method and apparatus for photodynamic therapy that can reduce or eliminate damage to epithelial tissue in a controllable manner while allowing treatment of underlying targeted tissue.

OBJECTS AND SUMMARY OF THE INVENTION

Although various photosensitizer and ALA-induced PDT techniques provide an effective treatment for many conditions, accumulation of precursor photosensitizers and/or photosensitizers may generally not be selective. Thus, the precursor photosensitizer can metabolize into a photosensitizer in both surface tissue and underlying targeted tissue, thereby potentially causing unintended damage to non-targeted, healthy surface tissue during subsequent PDT treatment. Exemplary embodiments of the present invention provide methods and devices for preventing or reducing the extent or likelihood of unwanted damage to epithelial tissue, or other non-targeted tissues, during PDT.

In one aspect of the present invention, a method is provided for applying a precursor photosensitizer to an anatomical structure, and then applying a first inhibiting radiation to the anatomical structure. The first inhibiting radiation is configured to substantially reduce or eliminate the presence of a photosensitizer within a first region of the anatomical structure, such as a surface or epithelial region, by inhibiting or preventing formation of the photosensitizer from the precursor photosensitizer. A second radiation is then applied to the anatomical structure to produce a phototoxic species from the photosensitizer located in a second region of the anatomical structure. The first region may be substantially unaffected by the second radiation, and the second region can contain particular target sites which are to be damaged by the phototoxic species. Preferably, the first radiation is applied at a lower level (e.g., lower fluence and/or irradiance) than the second radiation. The first and second radiation can be applied at different wavelengths or wavelength bands (e.g., a first wavelength of the first inhibiting radiation can be shorter than a second wavelength of the second radiation).

In embodiments of the present invention, the first inhibiting radiation has a wavelength that is between about 320 nm and about 850 nm, or preferably between about 320 nm and about 450 nm, and the second radiation has a wavelength that is between about 380 nm and about 700 nm, or between about 470 nm and about 700 nm, or more preferably between about 625 nm and about 645 nm if, e.g., ALA, ALA derivatives, or porphyrins are used. Other wavelengths may be used as appropriate with different precursor photosensitizers.

In further embodiments of the present invention, the first inhibiting radiation is applied with an irradiance that is between about 0.01 mW/cm$^2$ and about 30 mW/cm$^2$ and a total fluence that is between about 1 and about 100 J/cm$^2$. The inhibiting radiation can be applied at any time prior to application of the second radiation, and is preferably applied within 30 minutes of application of the precursor photosensitizer (e.g., an ALA solution) to the tissue, or more preferably less than about 15 minutes after applying the precursor photosensitizer.

For example, exemplary embodiments of the present invention may be used for controlling the application of PDT induced using a precursor photosensitizer, and in particular for preventing damage to epithelial tissue, such as the epidermis, during PDT. A precursor photosensitizer, such as a porphyrin precursor, is administered to a targeted treatment site by topical application or injection. The precursor photosensitizer is absorbed through the surrounding tissue and into tissue at the targeted site, where it is generally metabolized and converted into a photosensitizer, such as a porphyrin. Formation of the photosensitizer is inhibited or prevented in epithelial tissue surrounding the targeted treatment site by application of an inhibiting radiation. The targeted site is then irradiated with a treatment radiation to activate the photosensitizer and damage tissue at the targeted treatment site, while epithelial tissue surrounding the targeted treatment site remains substantially unaffected. The treatment radiation is preferably applied within 30 minutes after exposure to the inhibiting radiation is stopped, or more preferably less than about 15 minutes after ending the application of the inhibiting radiation.

In further embodiments, metabolism of the precursor photosensitizer in non-targeted epithelial tissue surrounding the targeted treatment site is inhibited by exposing the tissue to electromagnetic radiation. For example, electromagnetic radiation that is highly absorbed and/or scattered by the epithelial tissue can be applied, such that a sufficient exposure dose of the radiation does not penetrate to the targeted site to any significant degree. Inhibition of the metabolism of the precursor photosensitizer is thereby confined to regions above a particular depth of the epithelial tissue, and the photosensitizer may still form and accumulate within the targeted site. Subsequent PDT treatment with application of a treatment radiation can lead to cellular damage or death within the targeted site, while leaving the epithelial tissue relatively undamaged because of a relative lack of photosensitizers therein.

In another embodiment, a method is provided for treating a disorder of the skin in a subject by administering 5-aminolevulinic acid to the subject and applying a first inhibiting radiation to the skin of the subject in an amount and duration sufficient to reduce protoporphyrin IX accumulation within the epidermis of the skin. A second radiation is then applied to the skin of the subject an amount and duration sufficient to produce a phototoxic species from the protoporphyrin IX located in dermis of the skin. The epidermis may be substantially unaffected by the second radiation, thereby treating the disorder of the skin in the subject. The first inhibiting radiation can, if desired, be applied continuously during the period of metabolism which occurs after administration of the 5-aminolevulinic acid or similar precursor photosensitizer.

In still further embodiments, a photobleachable compound such as, e.g., a porphyrin, is used as a photosensitizer. Such photosensitizers can be photobleached in non-targeted tissue by exposing the non-targeted tissue to electromagnetic radiation having an appropriate irradiance, fluence and wavelength to photobleach the agent without forming sufficient reactive oxygen species or otherwise causing cellular damage or death. The photosensitizer is thus "deactivated" (e.g., in a gentle manner) in certain tissue regions and can still accumulate within the targeted site. Again, subsequent PDT treatment leads to cellular damage or death within the targeted site, while leaving the epithelial tissue relatively undamaged because of the relative lack of photosensitizers therein. The radiation used to photobleach a compound is preferably provided at a lower fluence and/or irradiance than the radiation subsequently applied during PDT treatment. Properties of the lower fluence and/or irradiance can be selected for the first exposure to facilitate repair processes in the irradiated tissue and thereby allow the tissue to be spared. The wavelength of the photobleaching radiation may also be different than that of the PDT treatment radiation. For example, the photobleaching radiation may have a shorter wavelength than the PDT treatment radiation, such that it does not penetrate as deeply into the tissue, allowing unbleached compounds to remain in higher concentrations at deeper levels within the tissue. The delay time between applying the photosensitizer and applying the photobleaching light can be optimized to allow accumulation of photosensitizer in the target tissue as compared with the non-target tissue, as described in more detail below.

Photobleachable photosensitizers that may be used in embodiments of the present invention include, but are not limited to, a porphyrin, chlorin, porphycene, purpurin, texaphyrin, phthalocyanine, naphthalocyanine, bacteriochlorin, benzophenothiazine, tetracycline, methylene blue, and/or hypericin.

In certain embodiments, the first inhibiting radiation has a wavelength between about 320 nm and about 800 nm, or preferably between about 380 nm and about 420 nm. In other embodiments, the first inhibiting radiation is applied at an irradiance that is between about 0.1 mW/cm$^2$ and about 30 mW/cm$^2$, and a fluence that is between about 1 J/cm$^2$ and about 100 J/cm$^2$. In further embodiments, the second radiation has a wavelength between about 400 nm and about 900 nm, preferably between about 600 nm and about 800 nm, or even more preferably between about 625 nm and about 720 nm.

In a further aspect, embodiments of the present invention provide an apparatus for performing PDT treatment that avoids significant damage to epithelial tissue. The apparatus includes an inhibiting radiation source, which can be configured to prevent or reduce the formation of photosensitizers in the epithelial tissue above a targeted treatment site or, alternatively, to photobleach photosensitizers in certain regions of tissue near the targeted site. A treatment radiation source is provided, where the treatment radiation is configured to activate the photosensitizers located at the target site while leaving the epithelial tissue essentially unaffected because of the lack of photosensitizers in that tissue. A controller and delivery arrangement are also provided to control parameters associated with the inhibiting and treatment radiation sources, and to direct the radiations toward the tissue being treated. The apparatus may also include an arrangement configured to cool the surface of the tissue being treated. Optionally, a sensing device is provided to detect one or more characteristics of the tissue being treated, and to communicate with the controller such that the controller may vary one or more parameters of the inhibiting and/or treatment radiations based on the detected characteristics.

The inhibiting radiation can have a wavelength that is shorter than that of the treatment radiation, e.g., it may be green, blue or near-UV light. The inhibiting radiation may thus be scattered and absorbed more than the treatment radiation, such that the treatment radiation penetrates more deeply into the tissue than the inhibiting radiation. This difference in the radiation characteristics allows formation and accumulation of photosensitizers at target sites deeper within the tissue. For example, the inhibiting radiation can have a wavelength between about 320 nm and about 450 nm, or between about 380 and about 430 nm. In certain embodiments, the inhibiting radiation has a longer wavelength, and may include green, yellow, orange or even red light at wavelengths, fluences and/or irradiances capable of suppressing accumulation of photosensitizer during metabolism of the precursor photosensitizer used. For example, the inhibiting radiation may have a wavelength between about 320 nm and about 850 nm.

Characteristics of the treatment radiation are generally selected such that it can penetrate the tissue to a sufficient depth to reach the target sites. The treatment radiation can thus have, for example, a wavelength between about 630 nm and about 640 nm. The treatment radiation generally has a higher fluence and/or irradiance than the inhibiting radiation.

In further embodiments, cooling and/or radiative heating of the tissue being treated is provided. Cooling can be performed before, during and/or after application of the inhibiting radiation and/or treatment radiation. Such cooling can reduce discomfort during the PDT procedure, and may also further inhibit metabolism of pre-photosynthesizers in epithelial tissue. Radiative heating provided prior to application of the treatment radiation can enhance accumulation of photosensitizers at target sites to promote more effective treatment.

Embodiments of the present invention can be used to treat various conditions, including hair removal, acne, tumors, cysts, malformed blood vessels, cutaneous nevi, adnexal tumors, syringomas, cutaneous T cell lymphomas, squamous carcinomas, basal cell carcinomas, or cutaneous warts.

These and other objects, features and advantages of the present invention will become apparent upon reading the following detailed description of embodiments of the invention, when taken in conjunction with the appended claims.

BRIEF DESCRIPTION OF THE DRAWINGS

Further objects, features and advantages of the invention will become apparent from the following detailed description taken in conjunction with the accompanying figures showing illustrative embodiments of the invention, in which:

FIG. 9b is a schematic illustration of exemplary absorption behavior of a radiation beam that is provided at an acute incident angle to the tissue surface shown in FIG. 9a.

Figure 1:
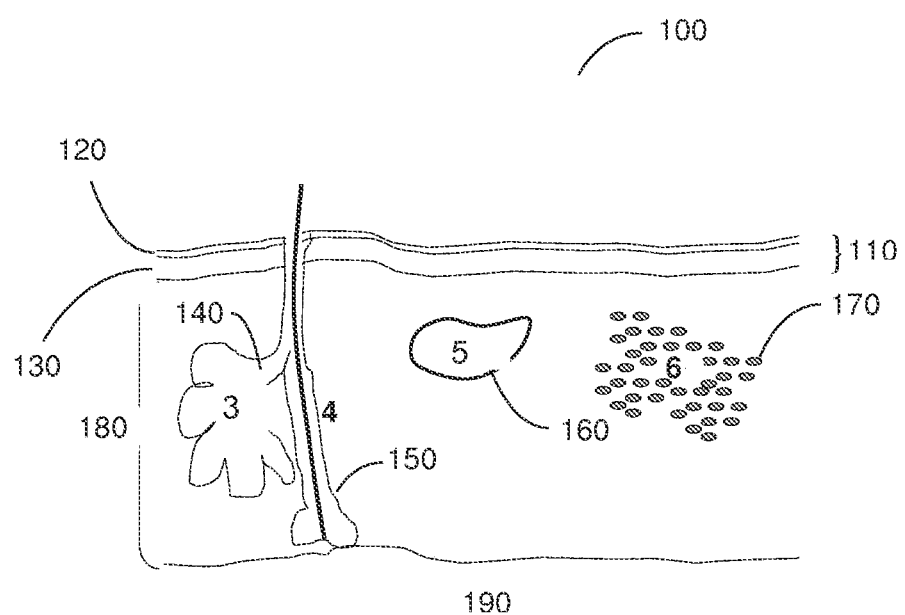
FIG. 1 is an exemplary cross-section of a portion of an anatomical structure showing several features of skin tissue.

While the present invention will now be described in detail with reference to the figures, it is done so in connection with the illustrative embodiments.

DETAILED DESCRIPTION

Definitions

As used herein, the phrase "anatomical structure" refers to, but is not limited to, a complex structure or system of the body having multiple layers and/or regions.

As used herein, the phrase "inhibiting radiation" refers to, but is not limited to, radiation provided at a suitable wavelength and in an amount and duration sufficient to: 1) reduce conversion of a precursor photosensitizer into a photosensitizer, or 2) photobleach a photosensitizer. The effects of such radiation may be more easily controlled by administering the radiation at a low level of irradiance and fluence.

As used herein, the term "photobleach" refers to, but is not limited to, treatment of a photosensitizer with an optical radiation in a spectrum that can be absorbed by the photosensitizer, but may not be of a sufficient excitation wavelength (e.g., the optical radiation causes little or no phototoxic species to be produced).

As used herein, the term "photosensitizer" refers to, but is not limited to, a photoactivatable compound that can produce a reactive species (e.g., singlet oxygen, free radicals, reactive excited state or cleavage products of the photosensitizer) which may have a toxic effect on a cell, cellular component or biomolecule.

As used herein, the phrase "precursor photosensitizer" refers to, but is not limited to, any agent or prodrug that can be converted in vivo (e.g., metabolically) into a photosensitizer.

As used herein, the phrase "phototoxic species" refers to, but is not limited to, a reactive species (e.g., singlet oxygen, free radicals, reactive excited state or cleavage products of the photosensitizer) which is produced from a photosensitizer in the presence of light administered at an excitation wavelength, where the reactive species can have a toxic effect on a cell, cellular component or biomolecule.

As used herein, to "reduce" as it refers to a photosensitizer, can indicate an at least about 1-fold (for example 1-, 2-, 3-, 4-, 5-, 10-, 20-, 30-, 40-, 50-, 60-, 70-, 80-, 90-, 100-, 1000-, 10,000-fold or more) less formation or accumulation of a photosensitizer in a subject upon treatment with inhibiting radiation as compared to without treatment. "Reduce" as it refers to a photosensitizer can also mean, e.g., at least about 5% (for example 5, 6, 7, 8, 9, 10, 15, 20, 25, 30, 35, 40, 45, 50, 55, 60, 65, 70, 75, 80, 85, 90, 95, 99 or 100%) less formation or accumulation of a photosensitizer in a subject upon treatment with inhibiting radiation than without treatment.

As used herein, the phrase "substantially unaffected" refers to, but is not limited to, a reduction or absence of damage (e.g., a visually undetectable amount), or non-lethal damage (e.g., oxidative damage) in a region or layer of an anatomical structure receiving inhibiting radiation prior to photodynamic therapy.

As used herein, the phrase "target tissue" refers to, but is not limited to, abnormal or unhealthy tissue, or a particular tissue structure such as, e.g., sebaceous glands in the skin, which may be selected for photodynamic therapy.

As used herein, the phrase "non-target tissue" refers to, but is not limited to, normal or healthy tissue or tissue structures or any other tissue in which photodynamic therapy is undesirable.

In this disclosure, "comprises," "comprising," "containing," "having," and the like have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Other definitions may appear in context throughout this disclosure.

Exemplary Embodiments

The methods and apparatus according to embodiments of the present invention utilize electromagnetic radiation to control and/or inhibit formation of a photosensitizer from a precursor photosensitizer administered to certain tissues for PDT procedures.

FIG. 1 shows an exemplary cross-section of a skin tissue 100 which can be treated using exemplary embodiments according to the present invention. The skin tissue 100 includes a superficial (e.g., epidermal) layer 110, which further includes a stratum corneum 120—a thin, nonliving outer layer of skin—and an epidermis 130, which is a superficial epithelial layer about 0.1 mm thick. The epidermis 130 is often the location of much of the perceived pain and undesirable side-effects that can accompany conventional PDT treatment. The dermal layer of skin 180 can be about 1-4 mm thick, and is located beneath the epidermis 130. The dermal layer (or dermis) 180 often contains certain targets which may be treated using PDT.

For example, a sebaceous gland 140 can be a primary target structure for treating acne using PDT. The sebaceous glands 140 are approximately 0.1-0.5 mm in diameter and are generally located about 1-3 mm below the epidermal layer 110. A hair-producing portion of a hair follicle 150 can be another target for the exemplary PDT treatment which can achieve hair removal. This portion of a hair follicle 150 can extend about 1-5 mm below the epidermal layer 110. A cellular structure 160 located within the dermis 180 can also be targeted and treated using PDT. Such structure 160 can include, e.g., a cutaneous tumor, a cyst, a nevus, a blood vessel or another biological feature. Cellular infiltrates 170 can represent still further targets, such as cutaneous T cell lymphoma cancer cells, which may also be treated using PDT. A fatty layer 190, located below the dermal layer 180, can also be targeted for PDT treatment in certain applications.

Figure 2:
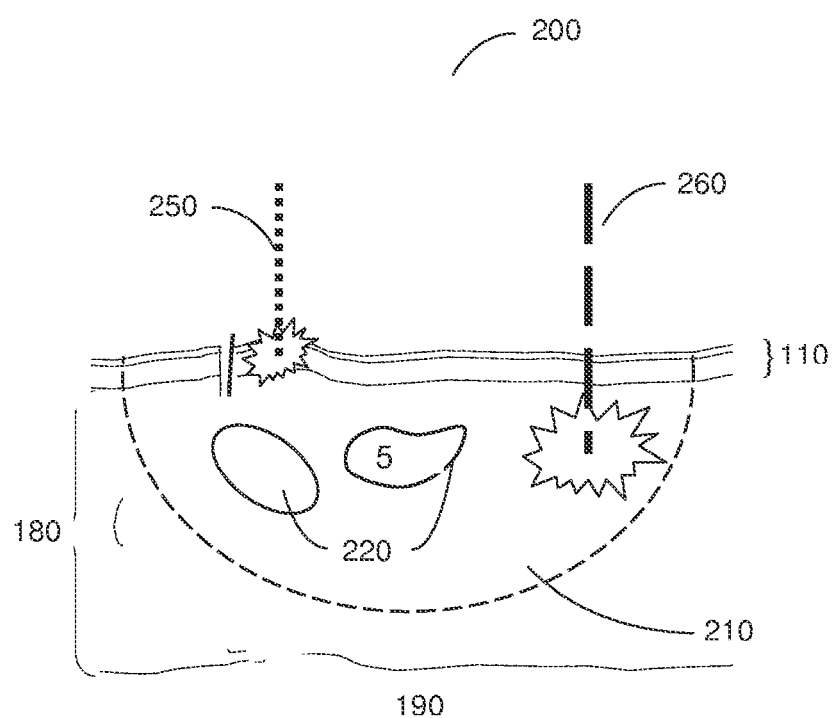
FIG. 2 is a schematic diagram of an exemplary procedure in accordance with exemplary embodiments of the present invention on the portion of an anatomical structure.

FIG. 2 is a schematic illustration of an exemplary technique applied to the tissue 200 according to exemplary embodiments of the present invention. A precursor photosensitizer is applied topically to a region of the tissue 200 to be treated, such that it is absorbed into the volume of a tissue portion 210 which includes target sites 220 to be treated. The tissue portion 210 containing the precursor photosensitizer generally includes a portion of both epithelial tissue (e.g., the epidermal layer 110) and the dermal layer 180 (and, optionally, a portion of the fatty layer 190).

For example, a precursor photosensitizer such as the porphyrin precursor ALA, can be topically applied to the tissue surface, e.g., epidermal tissue 110, above a targeted treatment site 220. The precursor photosensitizer is absorbed through such epidermal tissue 110 and into tissue 210 located at and around the targeted treatment site. ALA or other precursor photosensitizers can also be administered orally or by intravascular injection or by direct injection into tissue, e.g., by intradermal injection of an ALA solution.

An inhibiting radiation 250 is then directed onto the tissue portion 210. This inhibiting radiation 250 can have a relatively short wavelength (e.g., blue light) such that it is mostly absorbed in the superficial layer 110 and does not penetrate into the volume of tissue containing the target sites 220. The inhibiting radiation 250 can be applied during the time that the precursor photosensitizer is being metabolized to form a photosensitizer. Thus, it may selectively reduce or prevent formation of a photosensitizer in the superficial layer 110, while not significantly affecting formation of such photosensitizer in the target sites 220 and adjacent tissue. The photosensitizer can be selected such that, once formed, it preferentially accumulates at or around the target sites 220. Although only a single local beam of the inhibiting radiation 250 is shown in FIG. 2, the inhibiting radiation 250 is preferably applied over most or all of the area where the precursor photosensitizer was applied.

Parameters associated with the inhibiting radiation 250 (e.g., wavelength, total fluence, etc.) can be selected to inhibit formation of the photosensitizer to a particular depth within the tissue. The precursor photosensitizer located in the target sites 220, which is preferably exposed to a lower irradiance of the inhibiting radiation that does not substantially inhibit formation of the photosensitizer in the target sites 220, can metabolize into a photosensitizer, such as the protoporphyrin IX (PpIX).

A treatment radiation 260 is then directed onto the tissue portion 210. This treatment radiation 260 is preferably capable of penetrating the tissue to a depth containing the target sites 220, interacting with the photosensitizer and generating a reaction that can damage or destroy cells associated with the target sites 220. Upon the application of the treatment radiation 260 (e.g., light having an appropriate wavelength, fluence and irradiance), the photosensitizer absorbs such radiation and becomes phototoxic, releasing singlet oxygen or other intermediates that alter, damage or destroy cells within the target site. Although only a single local beam of the treatment radiation 260 is shown in FIG. 2, the treatment radiation 260 is preferably applied over most or all of the area where the precursor photosensitizer was applied. Because the formation of photosensitizers in the superficial layer 110 can be suppressed by the inhibiting radiation 250, the treatment radiation 260 may have little effect on the superficial layer 110, and cellular damage or death may be confined primarily to the target sites 220, and possibly to a lesser degree in other tissue regions below the superficial layer 110.

Using this exemplary technique, target sites 220 may be treated using PDT treatments, and damage to tissue in the superficial layer 110 can be avoided or reduced. This exemplary technique can also reduce pain experienced by a subject and/or post-treatment sensitivity of the superficial layer 110 to general exposure to light.

Exemplary embodiments of the present invention can be used for various applications such as, e.g., protection of the epidermis 110 during PDT treatment for removal of hair. For example, a precursor photosensitizer can be topically applied to the epidermal tissue surface 110 above a targeted treatment site 220, and an inhibiting radiation 250 is then directed to the targeted site 220. This radiation 250 may inhibit metabolism of the precursor photosensitizer within the epidermal tissue 110, while allowing the precursor photosensitizer to metabolize into a photosensitizer at hair follicles located in the target site 220. A treatment radiation 260 is then applied to the targeted treatment site 220 to destroy the hair follicles without damaging the epidermis 110. Surface cooling (e.g., contact or spray cooling) may optionally be provided before or during application of the treatment radiation. Such cooling can have an analgesic or anesthetic effect on the tissue being treated.

Parameters associated with the inhibiting radiation 250 and the treatment radiation 260 may be selected based on the precursor photosensitizer and photosensitizer used, the depth and type of the target sites 220, and other relevant factors. Such parameters can include, for example, irradiance, frequency, total fluence, pulse or continuous wave duration, and/or pulse repetition rate (frequency) of the applied radiation. The inhibiting radiation 250, e.g., may be a green or red light, and/or it can have a lower fluence and irradiance than the treatment radiation 260.

Figure 5:
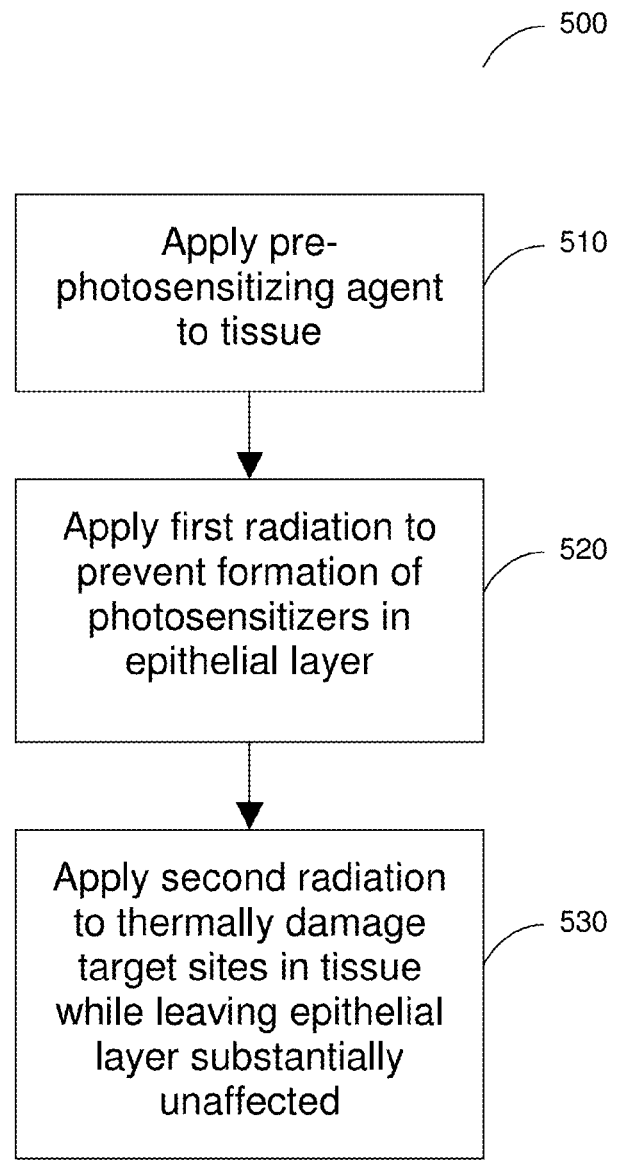
FIG. 5 is a flowchart of an exemplary method in accordance with exemplary embodiments of the present invention.

A flowchart of an exemplary method 500 in accordance with embodiments of the present invention is shown in FIG. 5. A precursor photosensitizer, such as a porphyrin precursor, is administered to a targeted treatment site (step 510). This can be achieved, for example, by topically applying the precursor photosensitizer to epithelial tissue surrounding the targeted site. The precursor photosensitizer is then absorbed through the surrounding tissue and into tissue at the targeted site, where it can be metabolized and converted into a photosensitizer, such as a porphyrin. Such metabolism of the photosensitizer is inhibited or prevented in epithelial tissue surrounding the targeted treatment site by application of an inhibiting radiation (step 520). The targeted site is then irradiated with a treatment radiation to activate the photosensitizer, e.g., to cause phototoxicity, at the targeted treatment site such that the epithelial tissue surrounding the targeted treatment site is substantially unaffected (step 530) because of a lack of photosensitizers there. The treatment radiation is preferably applied within 30 minutes after exposure to the inhibiting radiation is stopped, or more preferably less than about 15 minutes after ending the application of the inhibiting radiation.

Two significant time intervals relate to embodiments of the present invention. The first interval (the "inhibiting interval") is the time between application of the precursor photosensitizer to the tissue being treated and the initial exposure of the tissue to the inhibiting radiation. The second interval (the "treatment interval") is the time between when the inhibiting radiation exposure is stopped and the exposure of the tissue to the treatment radiation begins. These time intervals should be selected appropriately to allow the precursor photosensitizer to reach the target regions and metabolize there, while not allowing significant formation of photosensitizers in the tissue regions to be protected.

Studies of ALA metabolism and porphyrin accumulation rates have been performed in anterior ear skin of swine. Such tissue bears many similarities to facial skin tissue in humans with respect to size and location of relevant tissue layers and target regions such as hair follicles and sebaceous glands. Topical 20% ALA in a water/alcohol solution was applied to the skin tissue, and formation of photosensitizers was analyzed based on quantitative fluorescence analysis of porphyrins formed from the ALA.

Figure 8:
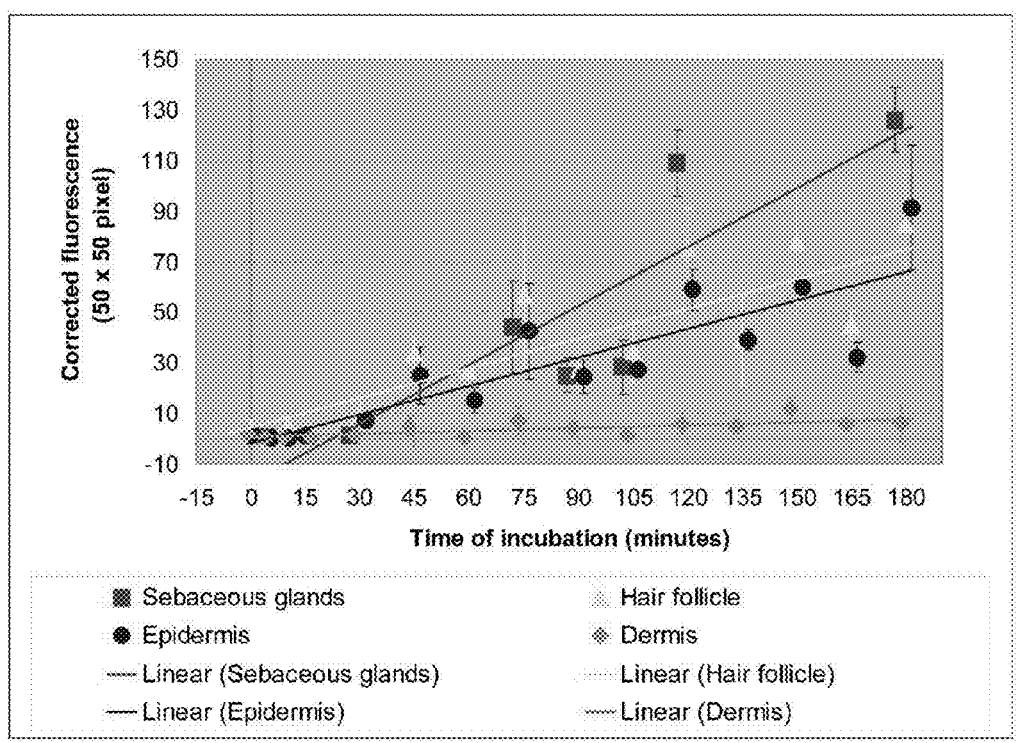
FIG. 8 is an exemplary graph of incubation times observed for metabolization of precursors photosensitizer.

Overall porphyrin fluorescence was not observed until about 30-45 minutes after application of the ALA solution, although epidermis fluorescence measurement was statistically significant after only 15 minutes following the ALA application. Between about 30 and 120 minutes following application of the ALA solution, epidermis, hair follicles, and sebaceous glands became progressively more fluorescent. Eccrine gland fluorescence was detected starting at about 30 minutes, and sebaceous glands showed fluorescence starting at about 45-75 minutes. Fluorescence in all sites reached a maximum intensity between about 75 and 180 minutes after application of the ALA solution. There was a trend for hair follicles and sebaceous glands to express stronger fluorescence compared with epidermis and eccrine glands. A summary of these results is presented in FIG. 8.

Based on these observations, it is generally preferable to apply the inhibiting radiation to tissue within about 30 minutes after topical application of ALA in accordance with certain embodiments of the present invention. An inhibition interval longer than about 30 minutes may allow undesirably significant formation of photosensitizers in the epithelial tissue. Preferably the inhibition interval is less than about 15 minutes to further prevent formation of significant amounts of photosensitizers in the epithelial layer. Shorter inhibition intervals may also be used.

The treatment interval corresponds to the delay between cessation of exposure of tissue to the inhibiting radiation and application of the treatment radiation. Based on the ALA metabolism observations described above and shown in FIG. 8, it is also generally preferable to apply the treatment radiation to tissue within about 30 minutes after the inhibiting radiation is stopped. A treatment interval longer than about 30 minutes may allow undesirable formation of photosensitizers in the epithelial layer from ALA still present in the tissue. Preferably the treatment interval is less than about 15 minutes to further prevent formation of significant amounts of photosensitizers in the epithelial layer. Even more preferably, the treatment radiation may be applied within a few minutes after exposure to inhibiting radiation is stopped, or even immediately thereafter.

In certain embodiments of the present invention, a photobleachable photosensitizer such as, e.g., Photofrin may be used instead of (or in addition to) a precursor photosensitizer. For example, the inhibiting radiation 250 can be applied to bleach a portion of the photobleachable photosensitizer. Subsequent application of the treatment radiation 260 can then induce damage or death in cells and tissue containing the unbleached photosensitizer. Application of the inhibiting radiation 250 can reduce or eliminate prolonged skin photosensitivity which can often be a side effect of PDT treatments.

In further embodiments, superficial porphyrin accumulation resulting from topical application of ALA may be suppressed by blue light exposure during ALA metabolism. For example, a topical solution of 20% ALA can be applied to a region of skin. The region of skin can then be exposed to low level irradiance 410 nm blue light to inhibit accumulation of porphyrins. This light can be applied during the period of ALA metabolism, e.g., immediately after the application of the topical ALA solution or later in time. It has been observed that exposure of skin to such low-intensity blue light (e.g., light having a wavelength of 415 nm) at an irradiance between about 10 mW/cm$^2$ and 30 mW/cm$^2$ during the period of ALA metabolism can provide almost complete clinical suppression of epidermal and/or superficial porphyrin synthesis, and does not itself induce a PDT reaction. Some suppression of photosensitizer formation was observed for irradiances between about 60 µW/cm$^2$ and 3 mW/cm$^2$. No clinical suppression was observed at less than about 30 µW/cm$^2$. Here, clinical suppression refers to a diminished response of the tissue to treatment radiation in subsequent PDT procedures.

Red light inhibiting radiation at a wavelength of 633 nm was observed to be less effective for clinical suppression of photosensitizer formation. Although such red light did not provide complete clinical suppression of superficial porphyrin synthesis, some clinical suppression was observed at irradiances between about 14 mW/cm$^2$ and about 40 mW/cm$^2$.

Other types of light, including but not limited to UV-A, blue, green, yellow and red light, may also be applied during the metabolism period to suppress porphyrin formation and/or accumulation. The suppression efficiency may depend in part on the absorption characteristics of the applied light. Such techniques can also be used with similar porphyrin precursor drugs, e.g., methyl-ester of ALA, that may also be suitable for photodynamic treatment of skin.

Several types of radiation or light sources may be used to provide the inhibiting radiation. Such sources include, for example, a fluorescent narrow-band light source, light emitting diodes ("LEDs"), lasers, arc lamps, or fluorescent and incandescent filtered lamps. In addition, pulsed or continuous sources can be used. In addition, the inhibiting radiation can be applied in various patterns, such that photosensitization is inhibited in only some parts of the non-target tissue. In some applications, the target tissue may be a fraction of a tissue region, while adjacent fractions are to be spared. Spatially "fractional" treatments using photothermal methods have been described, e.g., in Khan, M. H. et al, Lasers Surg Med 2005; 9999:1-11, and Manstein, D. et al, Lasers Surg Med 2004; 34:426-438-. Using inhibiting radiation in a pattern of exposure can create fractional photodynamic therapy.

Exemplary embodiments of the present invention may also be used to treat organs other than skin for which optical suppression of porphyrin synthesis in epithelial tissues may be useful. For example, when treating internal cancers with PDT, vital organs can be damaged because of insufficient selectively of the PDT reaction. Thus, the use of an inhibiting radiation or light during the incubation time can selectively suppress PDT reactions in certain areas, which may protect vital organs and reduce the generation of undesirable side-effects. The deeper tissue layer may contain the preferred targets for treatment such as hair follicles, sebaceous glands, eccrine glands, fat, cancer, blood vessels, nerves or other structures, whereas the superficial protected layer may be an epithelium such as the epidermis, oral or other mucosa, gastrointestinal or bladder epithelium, etc.

The treatment radiation is preferably selected such that it penetrates the tissue to a sufficient depth to reach the target sites. The rate of oxidative damage that occurs at target sites should be sufficient during application of the treatment radiation to cause at least the desired amount of damage to the target sites. In general, the rate of oxidative damage increases with the local concentration of photosensitizer in the targets, the local concentration of oxygen in the targets, and the rate of treatment radiation absorption by photosensitizer in the target sites. The inhibiting radiation can be administered in an amount and duration such that the concentration of the photosensitizer in the target sites is sufficient for at least a desired amount of damage to be produced at the target sites, while damage to the non-target sites should be substantially inhibited.

Embodiments of the present invention can be used with a variety of precursor photosensitizers including, e.g., enzyme-activated pre-photosensitizer constructs such as protease-sensitive oligopeptide conjugates, caged photosensitizers which are un-caged by an enzyme action, and porphyrin precursors. For example, ALA and similar compounds may be used as described in U.S. Patent Publication No. 2002/0099094. ALA can be used in a variety of forms, including in a pharmacologically equivalent form, such as an amide or ester, or as a salt, such as hydrochloride salt, and it can be topically applied to a tissue (e.g., skin) surface surrounding a targeted treatment site which may underlie epithelial tissue at the skin surface. ALA (e.g., 5-aminolevulinic acid) is converted in vivo to a photoactivatable compound, protoporphyrin IX (PpIX).

The wavelength of photoactivating light for protoporphyrin IX is generally in the range of between about 625 and 670 nm, or more preferably between about 625 and 640 nm. The fluence and irradiance range appropriate for treatment radiation can depend on the concentration of the photosensitizer in the target tissue, depth of the targets, and/or sensitivity of the particular type of targets involved. Fluence generally refers to a delivered optical energy per unit area, and can represent energy density delivered by an optical exposure. Irradiance generally refers to optical radiant power incident per unit area upon a surface, and may be expressed in watts per square meter. Preferred treatment wavelengths for some other photosensitizers can include, for example: chlorins (about 650-700 nm); porphycenes (about 635 nm); purpurins (about 630 to about 715 nm); texaphyrin (about 732 nm); phthalocyanines (about 670-680 nm), naphthalocyanines (about 780 to about 810 nm); and bacteriochlorins (about 650 to 800 nm).

Clinically, after topical application of 20% ALA to skin, followed by a period of metabolism between about 10 minutes and 24 hours, the range of 635 nm treatment radiation fluence is preferably between about 20 and about 200 J/cm$^2$, and the range of treatment radiation irradiance is preferably between about 20 and about 200 mW/cm$^2$.

In general, longer metabolism times are associated with lower fluence and irradiance requirements to achieve a therapeutic effect. After local injection of ALA, the local concentration can greatly exceed the local concentration achieved after topical application of ALA. Therefore, treatment fluence and irradiance ranges may generally be lower after administration of ALA or other pre-photosensitizers or photosensitizers by parenteral or local injection.

In other exemplary embodiments, the photosensitizer is photobleached upon exposure to selected inhibition radiation. For example, many photosensitizers used for PDT can also be destroyed by the reactive oxygen species produced during light exposure, a process which may be referred to as photobleaching. Cells may be able to tolerate a certain low dose of oxidative damage, because cells possess antioxidant and repair mechanisms. For cellular target sites to be irreversibly damaged during PDT, the rate of oxidative damage should exceed the rate of oxidative repair in target cells and achieve an amount of damage needed for cell killing by, for example, necrosis or apoptosis. In contrast, photobleaching is often irreversible. A low rate of photobleaching can therefore be used to prevent accumulation or reduce the concentration of the photosensitizer in the non-target sites, by administration of the inhibiting (photobleaching) radiation at a rate low enough that allows the non-target cells to repair.

Photobleachable photosensitizers include, for example, porphyrins, chlorins, some porphycenes, purpurins, phthalocyanines, naphthalocyanines, bacteriochlorins, benzophenothiazines, tetracyclines, methylene blue, hypericin, flavines, and derivatives thereof, either as free agents or in combination with specific delivery agents such as in liposomes or as photosensitizer conjugates with targeting molecules, such as peptides, receptor ligands or antibodies.

Accordingly, in one exemplary embodiment, relatively low-level light exposure is used for photobleaching of a photosensitizer in a non-target tissue, while allowing a sufficient amount of photosensitizer to remain in the target cells. This can be done, for example, in a superficial non-target epithelial layer by prolonged exposure to low-level short wavelength light, which harmlessly photobleaches in the non-target upper tissue layer but not in a deeper target layer.

Across the optical spectrum from about 320 nm to about 1200 nm, shorter wavelengths tend to penetrate less deeply than longer wavelengths due to optical scattering and absorption as described, e.g., in Anderson, R. R. et al., J Invest Dermatol 1981; 77:13-19. For example, the penetration of radiation having wavelengths between about 380 to 420 nm (e.g., UVA and deep blue light) into human skin is less than the penetration at wavelengths between about 620 to 700 nm (e.g., red light), due to relatively stronger scattering by dermal collagen, stronger absorption by epidermal melanin, and stronger absorption by hemoglobins in blood vessels. Attenuation by scattering and absorption within tissue can lead to an approximately exponential overall loss of irradiance with depth. Near the tissue surface, a maximum of irradiance may be present within the tissue at a depth of approximately $1/\mu_s$, where $\mu_s$ is an effective scattering coefficient. For example, using ALA or ALA derivatives as a pre-photosensitizer, and/or using porphyrins and chlorins as photobleachable photosensitizers, a wavelength of about 380 to about 420 nm may be a preferred wavelength for the inhibiting radiation. These agents involve a photosensitizer with strong Soret absorption band in this wavelength region.

In an exemplary embodiment of the present invention, an irradiance of about 1 mW/cm$^2$ at a wavelength between about 380 nm to about 420 nm can be used to inhibit porphyrin accumulation in epidermis (e.g., a superficial epithelium of skin) following topical application of 20% ALA in both animal and human skin. An irradiance less than about 1 mW/cm$^2$ of this wavelength region can also photobleach porphyrin and chlorin photosensitizers, at a rate which may be tolerable to the epidermis. The 1/e (37%) penetration depth of 380 to 420 nm radiation in Caucasian human skin is about 0.06-0.15 mm, which corresponds to an approximate thickness of human epidermis. For applications such as acne therapy, the epidermis is often a non-targeted tissue that is preferably spared from damage, whereas the target structures include sebaceous glands and sebaceous follicles in the underlying dermis. Sebaceous glands associated with acne are cellular target structures located about 1 mm below the surface. For example, with a target gland located about 1 mm deep, using an inhibiting radiation with a wavelength between about 380 to about 420 nm that has a 1/e penetration depth of about 0.1 mm, the target is about 10 times the 1/e penetration depth. The inhibiting radiation in this example is therefore attenuated by a factor of up to $e^{10}$ (e.g., about 0.00005 times the original intensity) by the time it reaches the target gland. The inhibiting radiation therefore can produce an irradiance in the epidermis (e.g., non-target tissue) which may be thousands of times greater than the irradiance in the sebaceous gland (e.g., target tissue). The inhibiting radiation can inhibit accumulation and/or photobleach a photosensitizer in the epidermis at a rate which may be tolerable for the non-target epidermal tissue, while having a very small effect on accumulation of photosensitizer in the deeper target tissue. In contrast, the 1/e penetration depth of the treatment radiation having a wavelength between about 620 to 700 nm is about 0.5 to 0.75 mm in human skin. This depth corresponds roughly to the depth of the target tissue. Such treatment radiation may be attenuated by a factor of only about 5 (and not, e.g., by orders of magnitude) before reaching the target. Because the inhibiting radiation step is used to greatly reduce or eliminate photosensitizer in the epidermis, the epidermis can be spared from significant damage during application of the treatment radiation.

Figure 9A:
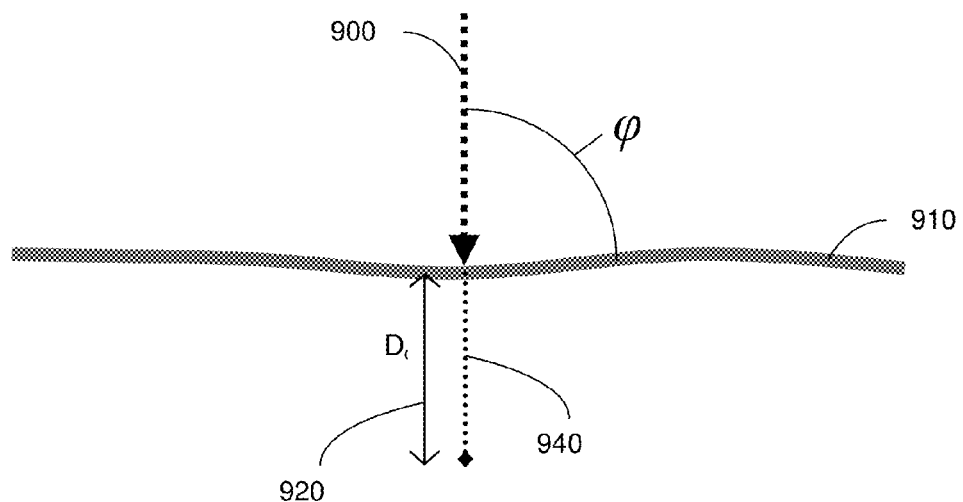
FIG. 9a is a schematic illustration of exemplary absorption behavior of a radiation beam that is approximately normal to a tissue surface.

FIG. 9a shows an application of a beam of radiation 900 that is approximately normal to the tissue surface 910. This corresponds to an incident angle of about 0°, or a complementary angle φ of about 90°. The penetration depth $D_o$ 920 associated with the beam 900 can refer to, e.g., a maximum depth at which at least a pre-defined amount of energy is locally absorbed by tissue. As described herein above, the depth $D_o$ 920 can depend on the wavelength of the radiation beam 900. For example, a desired depth $D_o$ 920 can be specified for a particular treatment by appropriate selection of a wavelength for the inhibiting and/or treatment radiation.

Figure 9B:
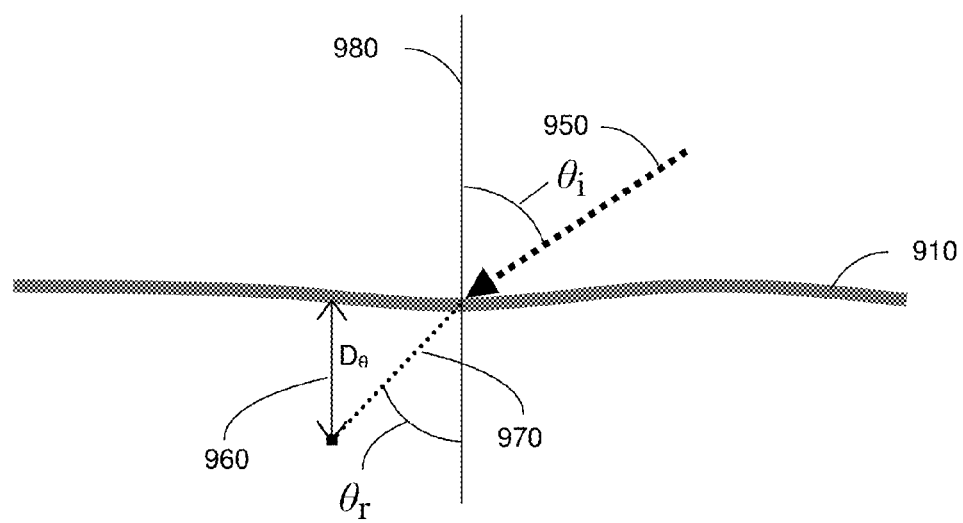

An effective penetration depth can also be controlled by varying the incident angle of applied radiation beam relative to the tissue surface. For example, FIG. 9b shows an exemplary application of an angled beam of radiation 950 that is provided at an incident angle $\theta_i$ of about 60° relative to the direction 980 normal to the tissue surface 910. The penetration depth $D_o$ 960 corresponding to the beam 950 that enters the tissue at a refracted angle $\theta_r$ will generally be smaller than the depth $D_o$ 920 associated with a normally incident beam 900 as shown in FIG. 9a. The depth $D_\theta$ can be expressed approximately as $D_\theta \sim D_o \cos(\theta_r)$, or $D_\theta \sim D_o(1-\sin^2(\theta_i)/n^2)^{1/2}$ based on Snell's law, where n is the index of refraction of skin tissue relative to air (or another adjacent medium, such as a sapphire plate, glass, etc.). The value of n for skin relative to air is approximately 1.3, which is similar to the value for water. Thus, the absorption path 970 within the tissue is generally not parallel to the incident angled beam 950, and can project at a slightly steeper angle into the tissue due to refraction. The approximate relationship $D_\theta \sim D_o(1-\sin^2(\theta_i)/n^2)^{1/2}$ also assumes that the local absorption behavior within the tissue along the path 970 is similar to the local absorption behavior along the path 940 in FIG. 9a, e.g., the tissue along each path has similar absorption characteristics.

When applying an incident radiation at some angle incident angle $\theta_i$ with respect to a tissue surface, the fluence and/or irradiance of the applied radiation may be adjusted (e.g., reduced) appropriately to provide a volumetric density of absorbed energy that is comparable to that of a beam that is normal to the tissue surface. For example, if the beams 900, 950 shown in FIGS. 9a and 9b have the same fluence, then the amount of energy absorbed by the tissue within a depth $D_o$ 920 in FIG. 9a would be absorbed within a shallower depth $D_o$ shown in FIG. 9b. To provide a comparable local density of energy absorption within the tissue, the fluence and irradiation of the incident angled beam 950 may be reduced by a factor of approximately $(1-\sin^2(\theta)/n^2)^{1/2}$. Although depth variations of tissue composition and/or presence of target structures within the tissue may affect local absorption characteristics, the factor of $(1-\sin^2(\theta)/n^2)^{1/2}$ can provide a basis for predicting effective penetration depth $D_o$ 960 and for maintaining a relatively constant density of energy absorption when applying a radiation beam 950 at an incident angle θ, as shown in FIG. 9b. The value of n may also be less than unity if the incident beam passes through another medium that has an index of refraction greater than that of skin. Other factors such as, e.g., polarization or reflectance at the interface between the media, can also affect the effective density of energy absorbed within the tissue. Such effects are described in more detail, e.g., in U.S. Pat. No. 6,529,543.

Photosensitizers and precursor photosensitizers can be administered in a pharmaceutically acceptable excipient, such as water, saline, aqueous dextrose, glycerol, or ethanol. The compositions may also contain other medicinal agents, pharmaceutical agents, carriers, and/or auxiliary substances such as wetting or emulsifying agents, and/or pH buffering agents. The photosensitizer or pre-photosensitizer can also be delivered by nanoparticles, microsponges, or other drug carriers.

Standard texts, such as Remington: The Science and Practice of Pharmacy, 17th edition, Mack Publishing Company, incorporated herein by reference, can be consulted to prepare suitable compositions and formulations for administration, without undue experimentation. Suitable dosages can also be based upon the text and documents cited herein. A determination of the appropriate dosages can be provided by one of ordinary skill in the art based on the parameters and criteria described herein.

A "therapeutically effective amount" refers to, but is not limited to, an amount sufficient to effect a beneficial or desired clinical result. In terms of treatment, an effective amount generally refers to an amount that may be sufficient to palliate, ameliorate, stabilize, reverse or slow the progression of a disorder (e.g., a skin disorder). A therapeutically effective amount can be provided in one or a series of administrations or doses. The effective amount may generally be determined by a physician on a case-by-case basis.

Several factors are typically taken into account when determining an appropriate dosage for in vivo therapeutics or diagnostics. These factors can include, for example, age, sex and weight of the patient, the condition being treated, the severity of the condition and/or the form of the antibody being administered.

The dosage of photosensitizer compositions for systemic administration typically range from about 0.1 to about 10 mg/kg. Methods for administering photosensitizer compositions are described, for example, in U.S. Pat. Nos. 5,952,329, 5,807,881, 5,798,349, 5,776,966, 5,789,433, 5,736,563, 5,484,803, 5,234,940 and by Sperduto et al. (1991) Int. J. Radiat. Oncol. Biol. Phys. 21:441-6; and Walther et al. (1997) Urology 50:199-206. Such dosages may vary, for example, depending on whether multiple administrations are given, tissue type and route of administration, the condition of the individual, the desired objective and other factors. Administrations can be conducted infrequently, or on a regular (e.g., weekly) basis until a desired, measurable parameter is detected, such as diminution of disease symptoms. Administration can then be diminished, such as to a biweekly or monthly basis, as appropriate.

Photosensitizers used in accordance with embodiments of the present invention can be administered by a mode appropriate for the form of the composition. Available routes of administration include, e.g., subcutaneous, intramuscular, intraperitoneal, intradermal, oral, intranasal, intrapulmonary (e.g., by aerosol), intravenously, intramuscularly, subcutaneously, intracavity, intrathecally or transdermally, alone or in combination with other pharmaceutical agents. Therapeutic compositions of photosensitizers can be administered by injection or by gradual perfusion. Compositions for oral, intranasal, or topical administration can be supplied in solid, semisolid or liquid forms, including tablets, capsules, powders, liquids, and suspensions. Compositions for injection can be supplied as liquid solutions or suspensions, as emulsions, or as solid forms suitable for dissolution or suspension in liquid prior to injection. For administration via the respiratory tract, a preferred composition can be one that provides a solid, powder, or liquid aerosol when used with an appropriate aerosolizer device. Although not required, compositions may preferably be supplied in unit dosage form suitable for administration of a precise amount. Slow release or sustained release forms of such compositions may also be used, whereby a relatively consistent level of the active compound can be provided over an extended period.

Cooling of the epithelial tissue can also be applied in certain embodiments of the present invention. For example, the skin surface can be cooled after application of a precursor photosensitizer such that the epidermis has a temperature that is less than the temperature of the underlying targeted tissue. Cooling can be performed using conventional techniques and arrangements such as, e.g., cryogen spray cooling or conductive contact cooling. A lower surface temperature can further inhibit the precursor photosensitizer from metabolizing into a photosensitizer in the epithelial tissue as described, e.g., in U.S. Patent Publication No. 2004/0259855. Epithelial cooling can greatly reduce the metabolism rate in the epithelial tissue (e.g., in non-targeted tissue).

In further exemplary embodiments of the present invention, the inhibiting radiation may be applied in patterns to reduce or prevent formation of photosensitizers in certain regions of tissue. Such patterns may be provided across a portion of the epithelial tissue and/or can include different exposure depths within the tissue to be treated, e.g., by varying the wavelength and/or intensity or fluence of the inhibiting radiation. In this manner, certain regions of tissue can be spared from the effects of a subsequent PDT procedure which involves application of a treatment radiation.

In yet further embodiments of the present invention, formation and/or accumulation of porphyrin or other photosensitizing metabolite accumulation are optically suppressed prior to photodynamic therapy light exposure, e.g., during conversion of ALA, ALA-esters or other pre-photosensitizer drugs which may be applied topically, orally or systemically to tissue. A light source is used to provide inhibiting radiation at one or more wavelengths between, e.g., about 320 nm and 850 nm. Over this spectral range, shorter wavelengths tend to penetrate tissue to a lesser extent than longer wavelengths. Thus, wavelength can be one factor which may be varied to control the depth of a superficial tissue layer to be limited or protected from damage during PDT treatment. For epidermal protection, wavelengths from about 320 to 450 nm may be preferred. Sources of radiation providing such wavelengths can include, for example, LEDs, lamps, filtered lamps, or lasers.

The depth of a superficial layer or other tissue region in which photosensitizers are to be suppressed can also depend on the fluence of the inhibiting radiation applied. A very low irradiance and fluence of blue light, for example, may be sufficient to suppress porphyrin accumulation during metabolism of topically applied 20% aminolevulinic acid, ALA. An irradiance of about 0.1 mW/cm$^2$ of blue light (e.g., 400-430 nm) can provide a suppressing effect. Typical irradiance values for inhibiting radiation procedures using blue light are between about 1 mW/cm$^2$ and about 30 mW/cm$^2$. Typical fluence values which may be used for inhibiting radiation procedures are between about 1 J/cm$^2$ and about 100 J/cm$^2$. Such irradiance and fluence values chosen for a particular PDT procedure can vary with wavelength and the precursor photosensitizer used.

Figure 3:
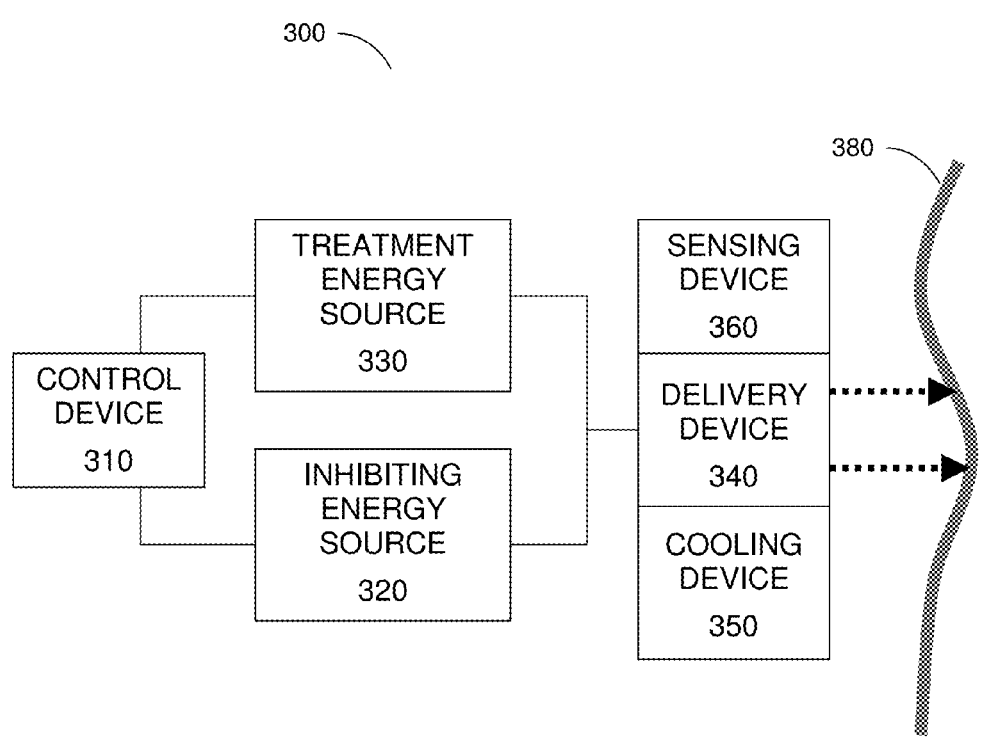
FIG. 3 is a block diagram of an exemplary apparatus/system which may be used in accordance with exemplary embodiments of the present invention.

In a further aspect, embodiments of the present invention provide a PDT treatment apparatus/system 300 which can be used to treat a tissue 380, as shown in FIG. 3. The PDT system 300 includes a control system 310 which is provided in communication with an inhibiting energy source 320 and a treatment energy source 330. The control system 310 can include a user interface for selecting and reviewing parameters of a treatment procedure, such as activation times, pulse rate and duration, radiation wavelength and/or fluence associated with the inhibiting and treatment energy sources 320, 330. Further control parameters may include timing and extent of cooling which may be provided by optional cooling device 350, positioning (including translational speed) of delivery device 340, and activation and/or feedback characteristics of optional sensing device 360.

The inhibiting energy source 320 is configured to generate an appropriate inhibiting radiation, as described herein. Such radiation can be provided, e.g., by a laser, one or more LEDs (such as an array of near-UV or blue LEDs), etc. The treatment energy source 330 is configured to generate an appropriate treatment radiation, as described herein. Such radiation can be provided, e.g., by a laser, one or more LEDs (such as an array of red or near-IR LEDs), etc. The inhibiting and treatment energy sources 320, 330 can be the same source, which may be configured with different parameters such as fluence, pulse frequency and duration, etc., and optionally with different wavelengths if the radiation source has a variable wavelength or filterable energy output. Alternatively, the inhibiting and treatment energy sources 320, 330 can be different sources as described above and may also be provided in separate enclosures.

The delivery device 340 may include optical components such as, e.g., optical fibers and/or mirrors which are configured to direct radiation from the inhibiting and treatment energy sources 320, 330 towards the tissue 380 to be treated. The delivery device 340 is optionally provided in a housing together with the inhibiting and treatment energy sources 320, 330 or otherwise integrated with one or both of them. For example, the delivery device 340 can include a reflective surface located behind or adjacent to one or more LEDs which may be provided as part of the energy sources 320, 330.

An optional cooling device 350 can also be provided with the exemplary PDT system 300. Such cooling device 350 can be integrated with the delivery device 340, or it may be a separate component. The cooling device 350 effectuates cooling of the tissue 380 to be treated using conventional cooling techniques including, for example, contact or conductive cooling, spray cooling (e.g., cryogenic spray) or convective cooling (e.g., a fan).

The exemplary PDT system 300 optionally includes a sensing device 360 that is configured to detect, for example, temperature and/or fluorescence of the tissue 380 being treated. The sensing device 360 can also be configured to detect a relative translational speed of the delivery device 340 with respect to the tissue surface 380, if the delivery device 340 is scanned or otherwise translated over the tissue 380 during the PDT procedure. The sensing device 360 is provided in communication with the control system 310, such that adjustment of various parameters (e.g., duration and timing intervals, pulse rate and/or fluence of the inhibiting and/or treatment radiation) can be affected by one or more conditions sensed by the sensing device 360.

In further embodiments, the exemplary PDT system 300 is powered by a portable electrical source such as a battery pack, which allows the entire PDT treatment to be performed at various locations within or outside of a clinical setting.

Figure 4:
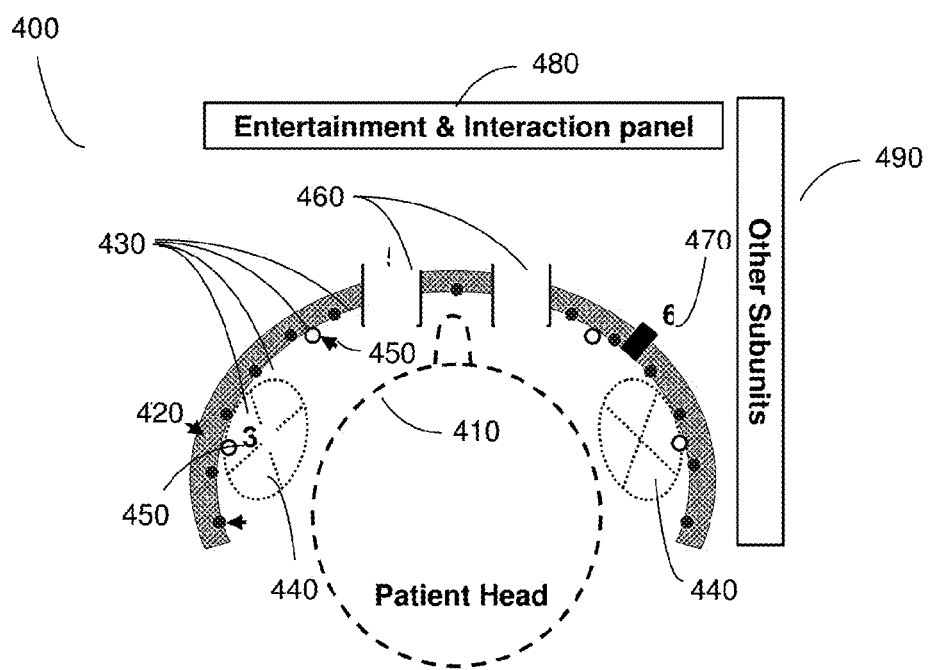
FIG. 4 is a schematic diagram of a further exemplary system which may be used in accordance with exemplary embodiments of the present invention.

In a further embodiment, an exemplary apparatus/system 400 configured to provide PDT treatment of facial skin 410 with optical photosensitizer inhibition is shown in FIG. 4. A topical solution of ALA, methyl ester of ALA, a similar photosensitizing precursor drug, or any photobleachable PDT agent is first applied to the skin 410 to be treated. The apparatus/system 400 includes a support structure 420 which partially or completely surrounds the skin 410 to be treated. Several treatment energy sources 430 may be located on the supporting structure 420. These treatment sources 430 can include, for example, an array of LEDs (e.g., LEDs having a wavelength between about 630 and 640 nm) or similar radiation sources. The apparatus/system 400 also includes one or more photoinhibition sources 450 affixed to the support structure 420, which may include an array of near-UV or blue LEDs (e.g., LEDs having a wavelength between about 380 and 430 nm).

The apparatus/system 400 optionally includes one or more cooling and/or warming devices 440 such as, e.g., a fan, a cooling spray, a filtered incandescent lamp and/or an infrared LED. Such cooling and/or warming devices 440 may be mounted onto support structure 420 above and/or below the level of the sources 430, 450. Warming devices 440 may be used, e.g., to enhance absorption and accumulation of photosensitizers at targeted treatment sites (e.g., hair follicles or sebaceous glands).

The exemplary apparatus/system 400 can also include vision portals 460, which can allow a patient to view content displayed on entertainment panel 480 during treatment. One or more sensors 470 are optionally provided to detect skin temperature and/or fluorescence during PDT treatment. Such sensors 470 can include, for example, discrete detectors or camera detectors. The PDT apparatus/system 400 may further include other subunits 490 such as, e.g., a user interface for selecting and displaying treatment parameters, a control arrangement for controlling the parameters of the various components, etc. The physical layout of the various components in the exemplary apparatus/system 400 can be modified for treatment of other body sites, by providing certain components in separate housings and/or by articulation and/or placement of such components as needed.

In an exemplary PDT treatment procedure in accordance with certain embodiments of the present invention, the superficial layer to be protected is the epidermis, which may be about 0.1 mm thick. The target sebaceous glands to be treated (e.g., thermally damaged) are located on a patient's face, between about 1 to 3 mm deep in the underlying dermis layer of skin. First, the face is washed to remove oil and dirt. Various cleansers may be used including, e.g., abrasive cleansers that can increase uptake of topical medications by degreasing and scratching the skin surface.

A topical form of aminolevulinic acid (e.g., Levulan Kerastick®), a methyl ester of aminolevulinic acid (e.g. Metvx®), or another analog and/or PDT drug is then applied to at least one affected skin area. An occlusive, transparent plastic mask or covering such as, e.g., Saran® wrap or a transparent occlusive ointment may optionally be placed, sprayed or spread on the skin to further enhance penetration and uptake of the drug(s) to the intended target sites, e.g., sebaceous follicles. The occlusive ointment may contain volatile components such as water that can cool the skin surface.

The patient is positioned in front of (e.g., while sitting) or beneath (while lying down) an integrated exemplary treatment apparatus, such as those shown in FIGS. 3 and 4. The treatment apparatus can be programmed for "phase I" (e.g., pre-phototreatment) parameters. Such phase I parameters can include, for example, uptake and incubation time for the precursor photosensitizer, energy source settings for photo-inhibition of epidermal porphyrin accumulation, surface cooling settings for temperature-based suppression of epidermal porphyrin accumulation, radiant tissue heating settings to enhance porphyrin accumulation in the targeted sites, monitoring characteristics of skin temperature to control the cooling/heating devices for achieving a desired skin surface temperature, and/or monitoring of porphyrin fluorescence during or after it accumulates, etc.

The inhibiting radiation applied during phase I is preferably provided after an interval of less than about 30 minutes following application of the ALA or other PDT drug, or more preferably less than about 15 minutes following application of the precursor photosensitizer. Still shorter intervals may be even more preferable. As described above, longer intervals may allow initial metabolizing of the precursor photosensitizer to form photosensitizers in epithelial tissue regions where protection from PDT effects is desired.

"Phase II" (e.g., phototreatment) parameters may also be selected for a particular PDT treatment. Such phase II parameters can include, for example, fluences, irradiances, exposure times and/or wavelengths of the treatment energy to be delivered. Wavelength variation, if desired, may be achieved by using, for example, a mixed LED array, by filtering of a single broadband source, or by using multiple light sources including sources that can be delivered by fiber optics or fiber optic bundles. The treatment energy may be delivered with or without skin cooling; such exemplary cooling (e.g., by flowing air) can provide added comfort.

"Phase III" (e.g., post-phototreatment) parameters and conditions may also be selected. For example, during phase III, skin cooling may be continued for comfort and to reduce swelling, and post-treatment porphyrin fluorescence may be monitored to assess epidermal or target viability.

In accordance with certain exemplary embodiments, phase I is typically configured to be activated for about 30-240 minutes, or preferably about 90-180 minutes, but the duration may range from about 0-300 minutes or more. Radiation sources which may be used for photoinhibition of photosensitizer formation/accumulation in phase I include, for example, one or more near-UV or blue (e.g., 320-450 nm) LEDs, a filtered lamp or array, one or more diode lasers, etc. The photoinhibition radiation source may optionally be the same source used to generate radiation for PDT treatment during phase II, but with a lower fluence or irradiance being provided during Phase I as compared to phase II. For example, irradiance during Phase I using an array of 635 nm LEDs can be between about 0.01 and 1 mW/cm$^2$, whereas during phase II the irradiance using the same LEDs can be between about 50 and 100 mW/cm$^2$. However, it may be preferable to use different radiation sources for phase I and phase II.

Figure 7:
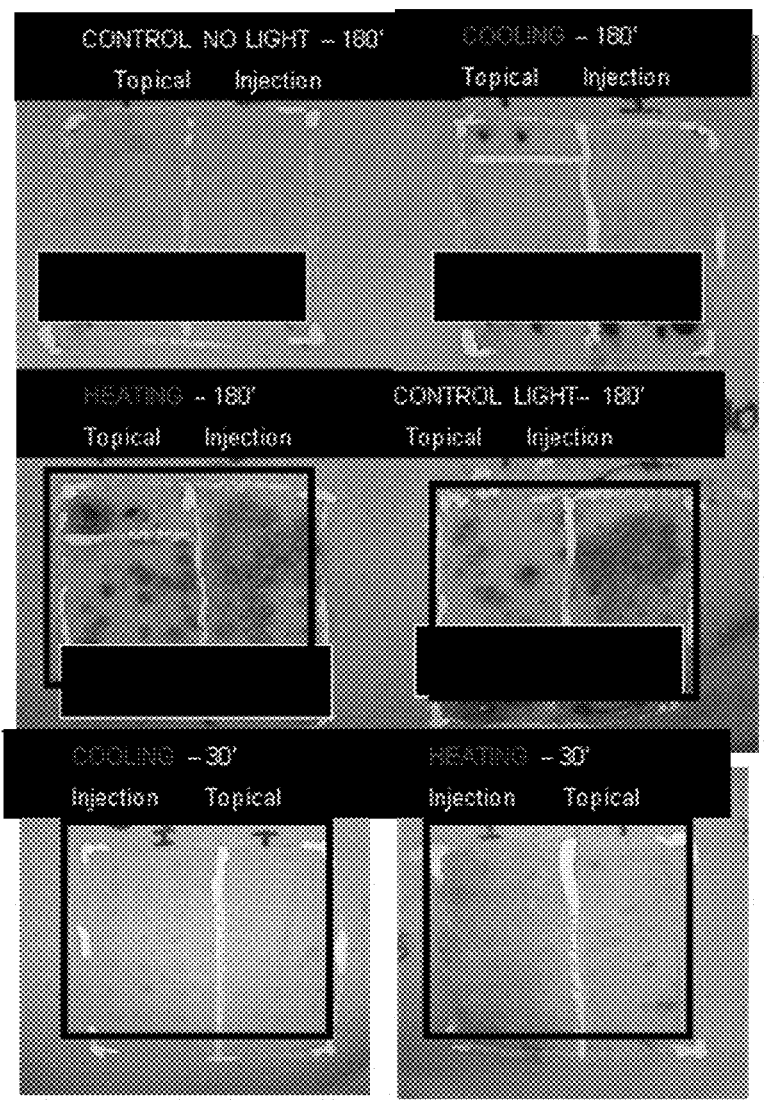
FIG. 7 depicts exemplary clinical photographs taken after 24 hours demonstrating temperature modulating PDT reaction under two different incubation times (180 minutes and 30 minutes), for 0.1% injected ALA and 20% topical ALA, with 632 nm LED irradiation (Omnilux®) applied to all sites (200 $J/cm^2$) after incubation.

A variety of techniques in addition to photoinhibition may be used during phase I to control or optimize the PDT treatment. For example, skin surface cooling may also be provided to increase comfort and/or to further suppress formation and/or accumulation of photosensitizers such as porphyrins near the skin surface, by partial inhibition of enzymes that convert ALA or methyl ALA to porphyrins, as shown in FIG. 7. Such cooling can be provided, e.g., by a cooling fan with or without a heat exchanger, and/or by evaporative techniques. Skin warming may also be provided during phase I using, e.g., a near infrared source such as filtered incandescent lamps or LEDs, or warmed air. Such warming during phase I may increase metabolism of ALA or methyl ALA to porphyrins in the targeted tissue sites, e.g., in sebaceous glands. Skin surface cooling, radiant skin warming, and photoinhibition may be used simultaneously or sequentially during phase I.

The treatment energy sources activated during phase II are preferably applied after an interval of less than about 30 minutes following application of the inhibiting radiation, or more preferably less than about 15 minutes following completion of the inhibiting radiation. Still shorter intervals may be even more preferable. As described above, longer intervals may allow further spreading and metabolizing of the precursor photosensitizer to form photosensitizers in tissue regions where protection from PDT effects is desired.

The radiation sources used to provide treatment radiation can include LED arrays, which may be preferable because of their simplicity, power, lifetime, and electrical and optical safety. The exemplary PDT system can also provide audio and/or visual indicators for procedure progress and/or warning signals such as speech indicating time, progress during each phase, and events that are about to occur. These indicators can also be used to request information such as degree of discomfort being experienced, and responses can be provided using manual inputs, voice-activated inputs or both. An entertainment device may also be provided to reduce patient boredom and/or to query the patient for information about treatment progress, sensations, preferences, etc.

During phase II, treatment exposure can often generate a tingling, burning, or painful sensation after a brief delay. An interface can be provided which includes the ability to reduce the treatment source irradiance, pause the treatment, increase skin cooling and/or air circulation on the skin, or distract the patient, based on input provided by a patient and/or operator. Treatment exposure time during phase II is typically in the range of about 10-45 minutes, but it may range from about 1 minute to about 120 minutes.

Other types of apparatus for PDT can be provided in accordance with embodiments of the present invention. For example, a portable treatment "patch" which includes a programmable photoinhibition device with or without cooling or warming (phase I), followed by a treatment light source activation device (phase II) with or without cooling can be constructed. Such a patch-based system can allow a patient complete mobility after application, injection or ingestion of the ALA, methyl-ALA, or other precursor photosensitizer. The patch-based system includes an energy supply, one or more radiation sources (such as LEDs), a processor or other device to control timing and application of the inhibition and treatment radiations, etc. These components can be provided in a small housing which can be affixed to the body over the area to be treated after application of the precursor photosensitizer.

For example, PDT procedures to treat acne can be provided by apparatus, systems and methods according to embodiments of the present invention in a physician's office, a treatment center, as a prescription home-use device, or as a non-prescription home use device. PDT treatment can be a labor-intensive office procedure. The embodiments of the present invention as described herein can allow a simpler and more flexible way to provide PDT treatment.

Optimized PDT techniques according to embodiments of the present invention can be practiced for skin diseases including acne, skin cancer, hair removal, nevus sebaceous, cutaneous nevi, adnexal tumors including syringomas, cutaneous T cell lymphoma, squamous and basal cell carcinomas, abnormal blood vessels, melanocytic and other cutaneous nevi, dysfunctional nerves, unwanted subcutaneous fat, and infections including fungal disease such as onychomycosis and viral disease such as cutaneous warts. For non-cutaneous applications, the methods and systems can be modified to fit the anatomical features involved. For example, the exemplary methods and apparatus/systems according to exemplary embodiments of the present invention may be used in gynecology for cervical and vaginal diseases, to treat oral and airway diseases, or gastrointestinal and internal diseases including neural tissues, cardiovascular, heart, endocrine, and muscle.

Embodiments of the present invention may also be used to treat skin cancer. For example, a precursor photosensitizer can applied to the skin and an inhibiting radiation can be applied to epidermal tissue above the targeted tumor site. The photoinhibition technique can allow the precursor photosensitizer to metabolize into a photosensitizer at the tumor site, thereby allowing the PDT to destroy the tumor cells while preventing damage to healthy non-cancerous epidermal tissue.

EXAMPLES

Example 1

Figure 6:
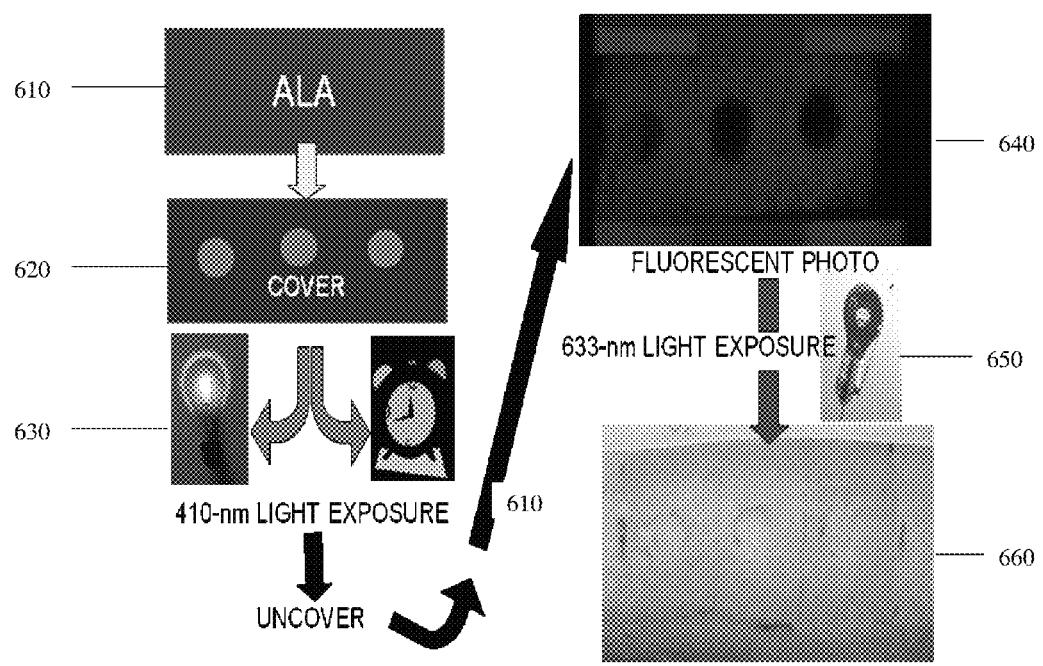
FIG. 6 depicts blue light inhibiting ALA-PDT.

Suppression of epidermal porphyrin accumulation by blue light exposure during ALA metabolism, in accordance with exemplary embodiments of the present invention, was tested in humans. With reference to FIG. 6, a 20% topical ALA solution was applied to human skin 610, covered with aluminum foil 620, while only some uncovered areas received 410-nm blue light (1.47 mW/cm$^2$) 630 during the incubation time. A fluorescent photo 640 was taken after 2 hours of incubation, and 632-nm light (100 J/cm$^2$) was then applied to all areas 650. A clinical photograph 660 was taken after PDT treatment.

Blue light exposure during the period of ALA metabolism was observed to suppressed porphyrin accumulation and subsequent PDT reactions. Inactivation of porphyrin synthetic enzymes or the pre-porphyrin metabolites, concurrent repair of oxidative damage during blue light exposure, and/or changes in cell signaling may contribute to this observed effect. Such findings indicate that exemplary embodiments of the present invention can provide a method to suppress porphyrin accumulation as a technique for controlling ALA-PDT. Low intensity blue light exposure during the period of ALA metabolism can suppress epidermal porphyrin synthesis, thus allowing for PDT of acne with less pain and/or fewer side effects.

When a skin surface is cooled, there can be a gradient of temperature such that ALA metabolism might favor the warm dermis. To examine this effect, cooling and heating plates were applied to skin after topical and injected ALA administration, and porphyrin synthesis and skin photosensitization were then determined. Skin cooling to a temperature less than about 20° C. was observed to significantly suppress conversion of epidermal ALA to porphyrins, thereby limiting the phototoxicity reaction of epidermis. Dermal porphyrin synthesis was observed to be partially suppressed when the skin surface temperature was 20° C., as shown, e.g., in FIG. 7. These results indicate that a device that cools the epidermis while simultaneously warming the dermis can selectively suppress unwanted epidermal porphyrins and could be used together with other porphyrin suppression methods in accordance with exemplary embodiments of the invention.

Example 2

In accordance with embodiments of the present invention, 20% topical ALA was applied to the skin of a pig. Nine different areas were divided and different attenuating films were placed over the skin during the entire incubation time (or the metabolism period). The attenuating films reduced the light transmittance allowing a range of irradiance varying from 100%, 56%, 44%, 35%, 26%, 21%, 19% to 17% of light during the incubation period.

Immediately after the drug application, a 410 nm blue light was irradiated through all the experiment sites at an irradiance of 2.6 mW/cm$^2$ for 3 hours. During this period, porphyrin accumulation was measured in each test area by digital fluorescence photography (~410 nm excitation, >600 nm emission), and microscopically determined by fluorescence microscopy of skin biopsies (8 mm diameter) obtained prior to light exposure. After the 3 hours of incubation, red light at 635 nm exposure with 200 J/cm$^2$ fluence was delivered at 100 mW/cm$^2$ irradiance, provided by an LED array source (Omnilux, PhotoTherapeutics LTD, Cheshire UK). Measurements and biopsies were repeated after 24 hours, prior to euthanasia.

The results show inhibition of porphyrin accumulation in all sites down to 17% light transmittance (0.4 mW/cm$^2$), but for the site that was covered during the blue light exposure.

Example 3

Embodiments of the present invention were used to treat a 23 year old female Asian patient exhibiting moderate to severe inflammatory acne (acne III-IV). The patient's recalcitrant acne was resistant to conventional treatments (oral and topical antibiotics, topic retinoids and benzoyl peroxide), and failed to respond to Accutane treatment (2 cycles). A 20% ALA solution (Dusa Pharmaceutics) was applied topically to the patient's face. The right side of the patient's face was covered with saran wrap and aluminum foil for 3 hours of incubation (to provide a conventional PDT treatment), while blue light at very low intensity (an inhibiting radiation) was applied to the left side of the patient's face for 3 hours (using a Clearlight at 90 W/cm$^2$, provided about 2 meters from the patient).

After the incubation period, both sides of the face were irradiated with red light treatment radiation (635 nm wavelength, at about 180 J/cm$^2$, using an Aktilite). During the red light irradiation, the patient indicated a subjective pain score of about 9-10 (on a 0-10 scale, with 0 being no pain, 5 being moderate pain, and 10 being maximum pain) on the right side of her face receiving conventional PDT treatment. On the optically inhibited (left) side, the patient indicated subjective pain scores of 3-4 during application of the same treatment radiation.

Immediately after the treatment, the patient exhibited a significant inflammatory reaction and persistent pain on the conventionally-treated (right) side, while the optically inhibited (left) side only exhibited mild inflammation and no pain. The conventionally-treated side evolved with areas of exudative and exulcerated lesions, especially near the nose, and crusting was observed. In contrast, the optically inhibited (left) side only exhibited mild hyperpigmentation.

After four weeks, both sides of the patient's face showed no new inflammatory acne, with subjective reduction of sebum noticed by the patient. Hyperpigmentation was observed on the right side treated with the conventional PDT technique, while no negative side effects were observed on the left side of the face, which was treated with an inhibiting radiation prior to application of the treatment radiation, in accordance with embodiments of the present invention.

The reduction in perceived pain during PDT treatment, and reduction or elimination of short-term and long-term adverse side effects which were observed by application of the inhibiting radiation prior to PDT treatment clearly suggest the advantages of such methods and apparatus for PDT techniques.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. In addition, all publications, patents and patent applications referenced herein are incorporated herein by reference in their entireties.

What is claimed is:

1. A method for applying radiation to an anatomical structure, comprising:
    providing at least one precursor photosensitizer to an anatomical structure;
    applying a first radiation having a wavelength in the range of about 320 nanometers to about 450 nanometers to a first region of the anatomical structure located above a target site, wherein the first radiation is configured to at least one of reduce or eliminate a presence or an effectiveness of a photosensitizer that results from the precursor photosensitizer within the first region of the anatomical structure; and
    applying a second radiation having a wavelength in the range of about 470 nanometers to about 700 nanometers to a second region of the anatomical structure that includes the target site, which is below the first region, the second radiation being configured to interact with the photosensitizer located in the second region of the anatomical structure to damage at least a portion of the second region,
    wherein the second radiation is applied after the first radiation, and
    wherein at least a portion of the first region is substantially unaffected by the second radiation.

2. The method of claim 1, further comprising cooling at least a portion of the anatomical structure prior to applying the second radiation.

3. The method of claim 1, wherein parameters of the first radiation are selected to photobleach the photosensitizer within the first region, and wherein the second radiation is configured to interact with the photosensitizer located in the second region to produce a phototoxic species.

4. The method of claim 1, wherein the precursor photosensitizer comprises a therapeutically effective amount of aminolevulinic acid to the subject;
    wherein properties of the first radiation are selected to reduce a protoporphyrin IX accumulation within the epidermis of the skin;
    wherein properties of the second radiation are selected to produce a phototoxic species from the protoporphyrin IX located in dermis of the skin; and
    wherein the epidermis is substantially unaffected by the second radiation, thereby treating the disorder of the skin in the subject.

5. The method of claim 1, wherein an irradiance and a fluence of the first radiation are smaller than an irradiance and a fluence of the second radiation.

6. The method of claim 1, wherein the first radiation is applied for at least about 30 minutes.

7. The method of claim 1, wherein the first radiation is applied at an irradiance that is in the range of about 0.01 $mW/cm^2$ to about 30 $mW/cm^2$.

8. The method of claim 1, wherein the first radiation is applied at a fluence that is in the range of about 1 $J/cm^2$ to about 100 $J/cm^2$.

9. The method of claim 1, wherein the second radiation is applied at a fluence that is in the range of about 20 $J/cm^2$ to about 200 $J/cm^2$.

10. A method for treating a condition of the skin, comprising:
    applying at least one precursor photosensitizer to a treatment region of skin tissue, the at least one precursor photosensitizer being configured to be metabolized by cells in the treatment region to form a photosensitizer;
    applying a first radiation to an epidermis region of the treatment region of skin tissue,
    wherein the first radiation is configured to at least one of reduce or eliminate a presence or an effectiveness of the photosensitizer within the epidermis region of the treatment region while formation of the photosensitizer in a dermis region of the treatment region continues;
    applying a second radiation to the dermis region of the treatment region, which is below the epidermis region, wherein the second radiation is configured to interact with the photosensitizer in the dermis region to damage at least a portion of the dermis region,
    wherein the second radiation is applied after the first radiation, and
    wherein at least a portion of the epidermis region is substantially unaffected by the second radiation.

11. The method of claim 10, wherein a time interval between applying the at least one precursor photosensitizer and applying the first radiation is less than about 30 minutes, and wherein a time interval between applying the first radiation and applying the second radiation is less than about 30 minutes.

12. The method of claim 10, wherein the first radiation is applied for at least about 30 minutes.

13. The method of claim 10,
    wherein the at least one precursor photosensitizer comprises at least one of aminolevulinic acid (ALA), a derivative of ALA, a methyl of ALA, a methyl-ester of ALA, an amide of ALA, an ester of ALA, and a salt of ALA,
    wherein applying the first radiation is in an amount and duration sufficient to reduce protoporphyrin IX accumulation within the epidermis region, and
    wherein applying the second radiation produces a phototoxic species from the protoporphyrin IX located in dermis region, wherein the epidermis region is substantially unaffected by the second radiation.

14. The method of claim 10, wherein parameters of the first radiation are selected to photobleach the photosensitizer within the first region, and wherein the second radiation is configured to interact with the photosensitizer located in the second region to produce a phototoxic species.

15. The method of claim 10, wherein the first radiation has a wavelength in the range of about 320 nanometers to about 450 nanometers.

16. The method of claim 10, wherein the second radiation has a wavelength in the range of about 470 nanometers to about 700 nanometers.

17. The method of claim 10, wherein an irradiance and a fluence of the first radiation are smaller than an irradiance and a fluence of the second radiation.

18. The method of claim 10, wherein the first radiation is applied at an irradiance that is in the range of about 0.01 mW/cm$^2$ to about 30 mW/cm$^2$.

19. The method of claim 10, wherein the first radiation is applied at a fluence that is in the range of about 1 J/cm$^2$ to about 100 J/cm$^2$.

20. The method of claim 10, wherein the second radiation is applied at a fluence that is in the range of about 20 J/cm$^2$ to about 200 J/cm$^2$.

* * * * *